(12) United States Patent
Barrett et al.

(10) Patent No.: US 12,262,917 B2
(45) Date of Patent: Apr. 1, 2025

(54) SPINAL CURVATURE MODULATION SYSTEMS AND METHODS

(71) Applicant: Auctus Surgical, LLC, San Francisco, CA (US)

(72) Inventors: John Barrett, San Francisco, CA (US); Murali Kadaba, Mountain View, CA (US); John Ashley, Danville, CA (US); Damien Shulock, San Francisco, CA (US)

(73) Assignee: Auctus Surgical, Inc., San Francisco, CA (US)

( * ) Notice: Subject to any disclaimer, the term of this patent is extended or adjusted under 35 U.S.C. 154(b) by 905 days.

(21) Appl. No.: 17/365,508

(22) Filed: Jul. 1, 2021

(65) Prior Publication Data

US 2021/0322060 A1 Oct. 21, 2021

Related U.S. Application Data

(63) Continuation-in-part of application No. 16/302,733, filed as application No. PCT/US2017/033592 on May 19, 2017, now Pat. No. 11,065,037.

(Continued)

(51) Int. Cl.
| | | |
|---|---|---|
| *A61B 17/70* | (2006.01) | |
| *A61B 17/00* | (2006.01) | |
| *A61B 17/56* | (2006.01) | |

(52) U.S. Cl.
CPC ...... *A61B 17/7022* (2013.01); *A61B 17/7016* (2013.01); *A61B 17/7032* (2013.01);
(Continued)

(58) Field of Classification Search
CPC ............ A61B 17/7016; A61B 17/7022; A61B 17/7032; A61B 2017/00221; A61B 2017/564
See application file for complete search history.

(56) References Cited

U.S. PATENT DOCUMENTS

| | | |
|---|---|---|
| 4,522,501 A | 6/1985 | Shannon |
| 4,537,520 A | 8/1985 | Ochiai et al. |

(Continued)

FOREIGN PATENT DOCUMENTS

| | | |
|---|---|---|
| CN | 103167839 A | 6/2013 |
| CN | 103781429 A | 2/2017 |

(Continued)

OTHER PUBLICATIONS

International Search Report and Written Opinion dated Jul. 28, 2017, in connection with PCT/US2017/033592, filed May 19, 2017.

*Primary Examiner* — Nicholas J Plionis
(74) *Attorney, Agent, or Firm* — Downs Rachlin Martin PLLC

(57) ABSTRACT

Spinal curvature modulation systems, methods and related devices and instrumentation are disclosed, which include a flexible tether, a tether tensioning unit and bone anchors for the flexible tether that allow the tether to be secured across multiple vertebrae in a region of treatment. When the flexible tether is attached to multiple vertebrae, it can be used to correct spinal deformities. Tension in the flexible tether is adjustable transcutaneously without invasive surgical procedures by use of remotely driven actuators, such as a magnet-driven motor, or by a small tool insertable through a small incision. Disclosed systems and methods thus allow for multiple adjustments of tether tension, and spinal curvature, over time without repeated, highly invasive, spinal surgeries.

21 Claims, 29 Drawing Sheets

Related U.S. Application Data

(60) Provisional application No. 62/338,763, filed on May 19, 2016.

(52) U.S. Cl.
CPC .............. *A61B 2017/00221* (2013.01); *A61B 2017/564* (2013.01)

(56) References Cited

U.S. PATENT DOCUMENTS

| | | | |
|---|---|---|---|
| 4,946,459 A | 8/1990 | Bradshaw et al. |
| 5,527,309 A | 6/1996 | Shelton |
| 6,510,345 B1 | 1/2003 | Van Bentem |
| 6,610,091 B1 | 8/2003 | Reiley |
| 6,849,076 B2 | 2/2005 | Blunn et al. |
| 6,971,143 B2 | 12/2005 | Domroese |
| 7,029,472 B1 | 4/2006 | Fortin |
| 7,441,559 B2 | 10/2008 | Nelson et al. |
| 7,481,841 B2 | 1/2009 | Hazebrouck et al. |
| 7,674,293 B2 | 3/2010 | Kuiper et al. |
| 7,763,053 B2 | 7/2010 | Gordon |
| 7,955,357 B2 | 6/2011 | Klester |
| 7,976,568 B2 | 7/2011 | Cheung et al. |
| 8,016,837 B2 | 9/2011 | Giger et al. |
| 8,057,472 B2 | 11/2011 | Walker et al. |
| 8,062,375 B2 | 11/2011 | Glerum et al. |
| 8,147,521 B1 | 4/2012 | Cornwall et al. |
| 8,162,979 B2 | 4/2012 | Sachs et al. |
| 8,187,303 B2 | 5/2012 | Tokish et al. |
| 8,197,490 B2 | 6/2012 | Pool et al. |
| 8,221,461 B2 | 7/2012 | Kuiper et al. |
| 8,382,756 B2 | 2/2013 | Pool et al. |
| 8,425,606 B2 | 4/2013 | Cowan |
| 8,449,543 B2 | 5/2013 | Pool et al. |
| 8,475,467 B2 | 7/2013 | Manninen |
| 8,518,120 B2 | 8/2013 | Glerum et al. |
| 8,568,457 B2 | 10/2013 | Hunziker |
| 8,679,183 B2 | 3/2014 | Glerum et al. |
| 8,685,098 B2 | 4/2014 | Glerum et al. |
| 8,709,054 B2 | 4/2014 | Lowry et al. |
| 8,734,488 B2 | 5/2014 | Pool et al. |
| 8,864,833 B2 | 10/2014 | Glerum et al. |
| 8,888,853 B2 | 11/2014 | Glerum et al. |
| 8,926,704 B2 | 1/2015 | Glerum et al. |
| 8,961,567 B2 | 2/2015 | Hunziker |
| 8,992,578 B2 | 3/2015 | Slivka et al. |
| 9,034,045 B2 | 5/2015 | Davenport et al. |
| 9,050,141 B2 | 6/2015 | Zhang et al. |
| 9,078,711 B2 | 7/2015 | Quick |
| 9,149,367 B2 | 10/2015 | Davenport et al. |
| 9,155,628 B2 | 10/2015 | Glerum et al. |
| 9,168,071 B2 | 10/2015 | Seme et al. |
| 9,186,258 B2 | 11/2015 | Davenport et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,144 B2 | 12/2015 | Stauber |
| 9,216,095 B2 | 12/2015 | Glerum et al. |
| 9,248,043 B2 | 2/2016 | Payne et al. |
| 9,277,950 B2 | 3/2016 | Buttermann |
| 9,333,009 B2 | 5/2016 | Kroll et al. |
| 9,339,299 B2 | 5/2016 | Hestad |
| 9,345,517 B2 | 5/2016 | Zhang et al. |
| 9,358,126 B2 | 6/2016 | Glerum et al. |
| 9,408,641 B2 | 8/2016 | Zhang et al. |
| 9,433,442 B2 | 9/2016 | Lindemann et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,504,502 B2 | 11/2016 | Kuiper et al. |
| 9,526,526 B2 | 12/2016 | Zhang et al. |
| 9,526,530 B2 | 12/2016 | Broman et al. |
| 9,549,824 B2 | 1/2017 | McAfee |
| 9,579,126 B2 | 2/2017 | Zhang et al. |
| 9,622,792 B2 | 4/2017 | Pool et al. |
| 9,681,899 B2 | 6/2017 | Artaki et al. |
| 9,717,537 B2 | 8/2017 | Gordon |
| 9,757,160 B2 | 9/2017 | Gordon |
| 9,770,266 B2 | 9/2017 | Hestad |
| 9,801,734 B1 | 10/2017 | Stein et al. |
| 9,924,970 B2 | 3/2018 | Gordon |
| 9,931,138 B2 | 4/2018 | Lynch et al. |
| 9,949,759 B2 | 4/2018 | Lynch et al. |
| 9,949,761 B2 | 4/2018 | Fening et al. |
| 9,949,841 B2 | 4/2018 | Glerum et al. |
| 9,980,755 B2 | 5/2018 | Murray et al. |
| 10,016,220 B2 | 7/2018 | Culbert |
| 10,016,529 B2 | 7/2018 | Bhat et al. |
| 10,130,395 B2 | 11/2018 | Leff et al. |
| 10,136,928 B2 | 11/2018 | Leff et al. |
| 10,154,912 B2 | 12/2018 | Glerum |
| 10,219,914 B2 | 3/2019 | Faulhaber |
| 10,226,242 B2 | 3/2019 | Roschak et al. |
| 10,226,281 B2 | 3/2019 | Lynch |
| 10,238,427 B2 | 3/2019 | Wentz et al. |
| 10,262,587 B2 | 4/2019 | Nathan et al. |
| 10,271,885 B2 | 4/2019 | Quach et al. |
| 10,314,619 B2 | 6/2019 | Roschak et al. |
| 10,368,919 B2 | 8/2019 | Pham et al. |
| 10,390,891 B2 | 8/2019 | Govary et al. |
| 10,624,679 B2 | 4/2020 | Murray et al. |
| 10,624,683 B2 | 4/2020 | Suddaby |
| 11,065,037 B2* | 7/2021 | Barrett ............... A61B 17/8869 |
| 2006/0058791 A1 | 3/2006 | Broman et al. |
| 2006/0064090 A1* | 3/2006 | Park ................... A61B 17/7005 606/259 |
| 2007/0179493 A1 | 8/2007 | Kim |
| 2008/0033436 A1 | 2/2008 | Song et al. |
| 2009/0112207 A1 | 4/2009 | Walker et al. |
| 2009/0275984 A1 | 11/2009 | Kim et al. |
| 2010/0228167 A1 | 9/2010 | Ilovich et al. |
| 2010/0249928 A1 | 9/2010 | Schwab |
| 2010/0318129 A1 | 12/2010 | Seme et al. |
| 2010/0324600 A1 | 12/2010 | Biyani |
| 2011/0106185 A1 | 5/2011 | Gil et al. |
| 2012/0283781 A1 | 11/2012 | Arnin |
| 2013/0030466 A1 | 1/2013 | Kuiper et al. |
| 2013/0253587 A1 | 9/2013 | Carls et al. |
| 2014/0094851 A1 | 4/2014 | Gordon |
| 2014/0128868 A1 | 5/2014 | Harrison et al. |
| 2014/0214096 A1 | 7/2014 | Koch |
| 2014/0277472 A1 | 9/2014 | Gray et al. |
| 2015/0039036 A1 | 2/2015 | Serhan et al. |
| 2015/0045794 A1 | 2/2015 | Garcia et al. |
| 2015/0105834 A1 | 4/2015 | Bilger et al. |
| 2015/0201973 A1* | 7/2015 | Lindemann ........ A61B 17/7053 606/279 |
| 2015/0313745 A1 | 11/2015 | Cheng |
| 2016/0051377 A1 | 2/2016 | Weiman et al. |
| 2016/0296361 A1 | 10/2016 | Leake et al. |
| 2016/0324547 A1* | 11/2016 | Miller ................ A61B 17/7032 |
| 2017/0095273 A1 | 4/2017 | Lynch et al. |
| 2017/0095275 A1 | 4/2017 | Lynch |
| 2017/0231661 A1 | 8/2017 | Bannigan et al. |
| 2018/0207002 A1 | 7/2018 | Glerum et al. |
| 2018/0221058 A1 | 8/2018 | Bilger et al. |
| 2018/0221061 A1 | 8/2018 | Charest et al. |
| 2019/0091372 A1 | 3/2019 | Bhat et al. |
| 2019/0142472 A1 | 5/2019 | Mire et al. |
| 2019/0150913 A1 | 5/2019 | Roschak et al. |
| 2019/0209211 A1 | 7/2019 | Charest et al. |
| 2019/0216507 A1 | 7/2019 | Bannigan et al. |
| 2019/0298417 A1 | 10/2019 | Barrett et al. |
| 2019/0326043 A1 | 10/2019 | Janna et al. |
| 2020/0022741 A1 | 1/2020 | Janda et al. |
| 2020/0030003 A1 | 1/2020 | Charest et al. |

FOREIGN PATENT DOCUMENTS

| | | |
|---|---|---|
| CN | 108703798 A1 | 10/2018 |
| CN | 209347191 U | 9/2019 |
| EP | 3225212 A1 | 10/2017 |
| EP | 3420989 B1 | 1/2020 |
| JP | 2015-512328 | 4/2015 |

(56) References Cited

FOREIGN PATENT DOCUMENTS

| | | | |
|---|---|---|---|
| JP | 6479006 | B2 | 3/2019 |
| JP | 6654559 | B2 | 2/2020 |
| KR | 10181194 | B1 | 8/2018 |
| WO | 2013062696 | A1 | 5/2013 |
| WO | 2013152257 | A1 | 10/2013 |
| WO | 2015021454 | A1 | 2/2015 |
| WO | 2017017770 | A1 | 7/2015 |
| WO | 2015168175 | A1 | 11/2015 |
| WO | 2017066226 | A1 | 4/2017 |
| WO | 2017100774 | A1 | 6/2017 |
| WO | 2017127532 | A1 | 7/2017 |
| WO | 2017132646 | A1 | 8/2017 |
| WO | 2017139785 | A1 | 8/2017 |
| WO | 2017201437 | A1 | 11/2017 |
| WO | 2020055874 | A1 | 3/2020 |

\* cited by examiner

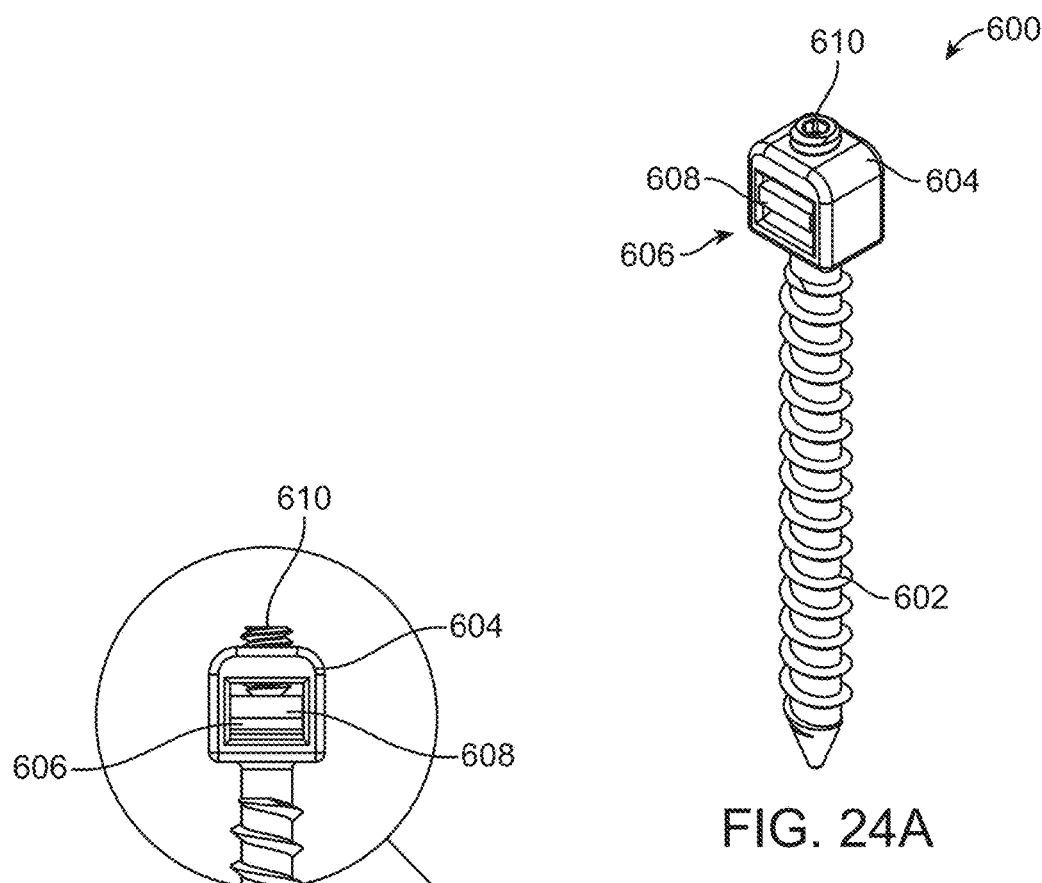
FIG. 24A
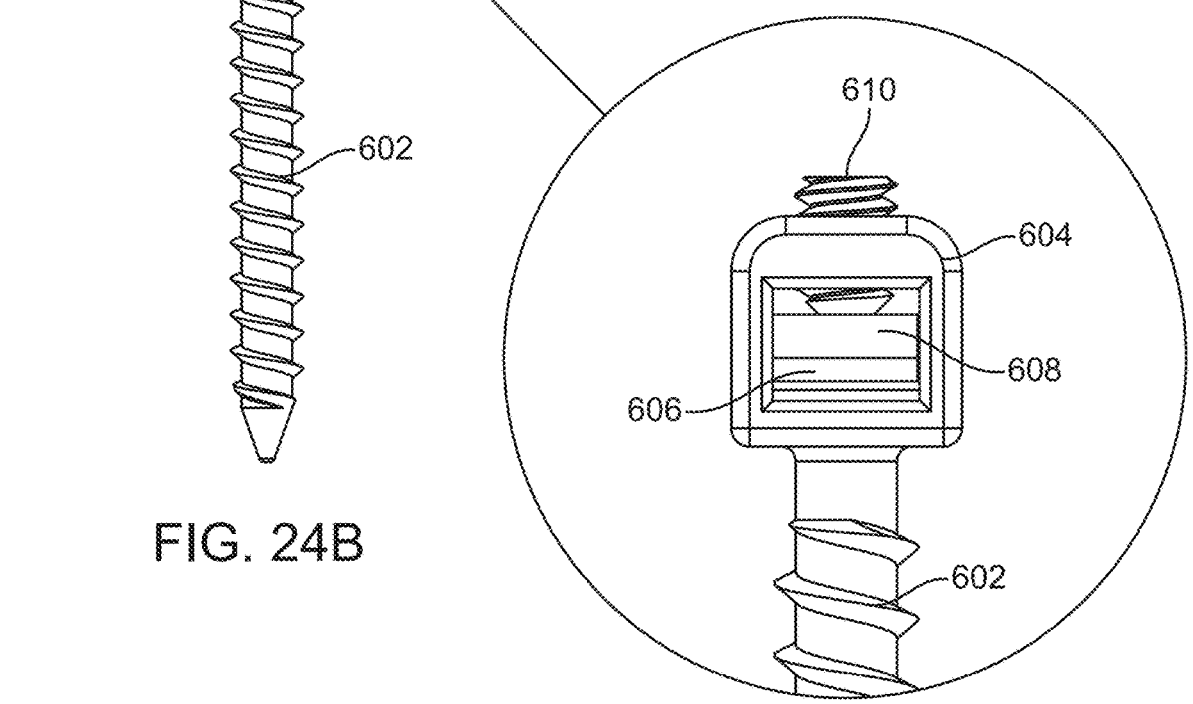
FIG. 24B
FIG. 24C

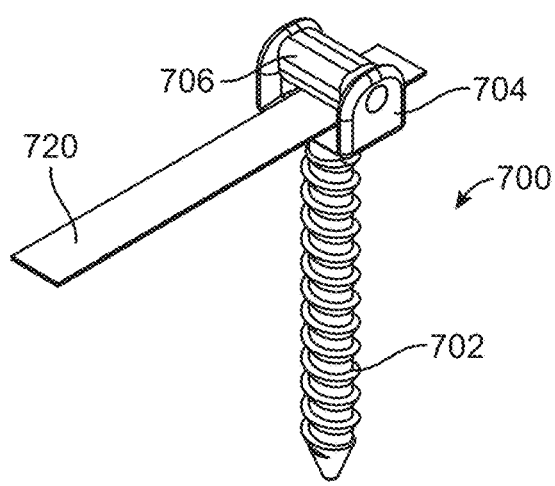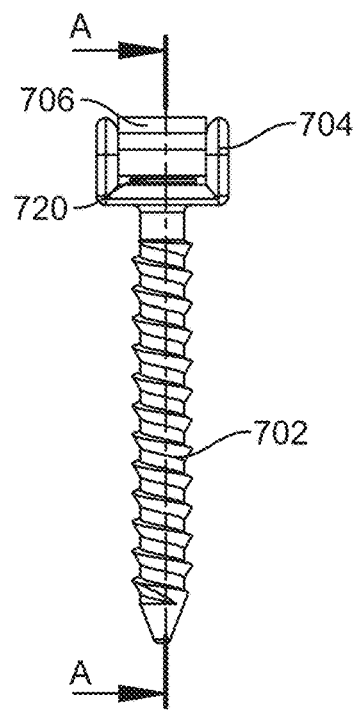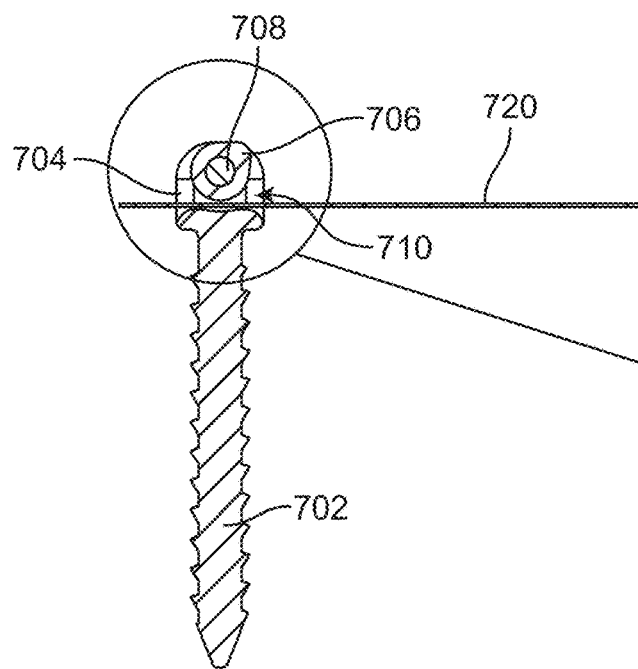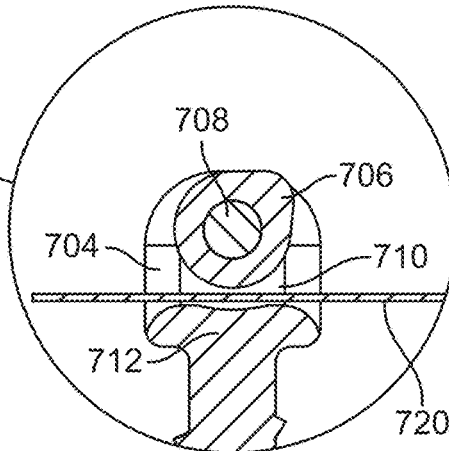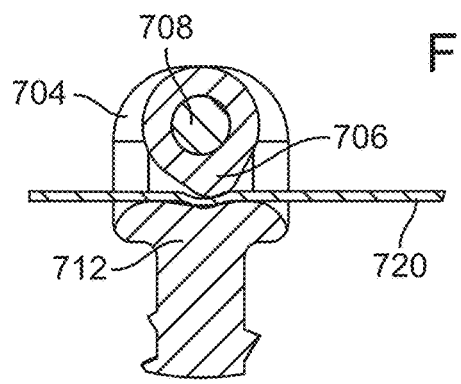
FIG. 25A
FIG. 25B
FIG. 25C
FIG. 25D
FIG. 25E

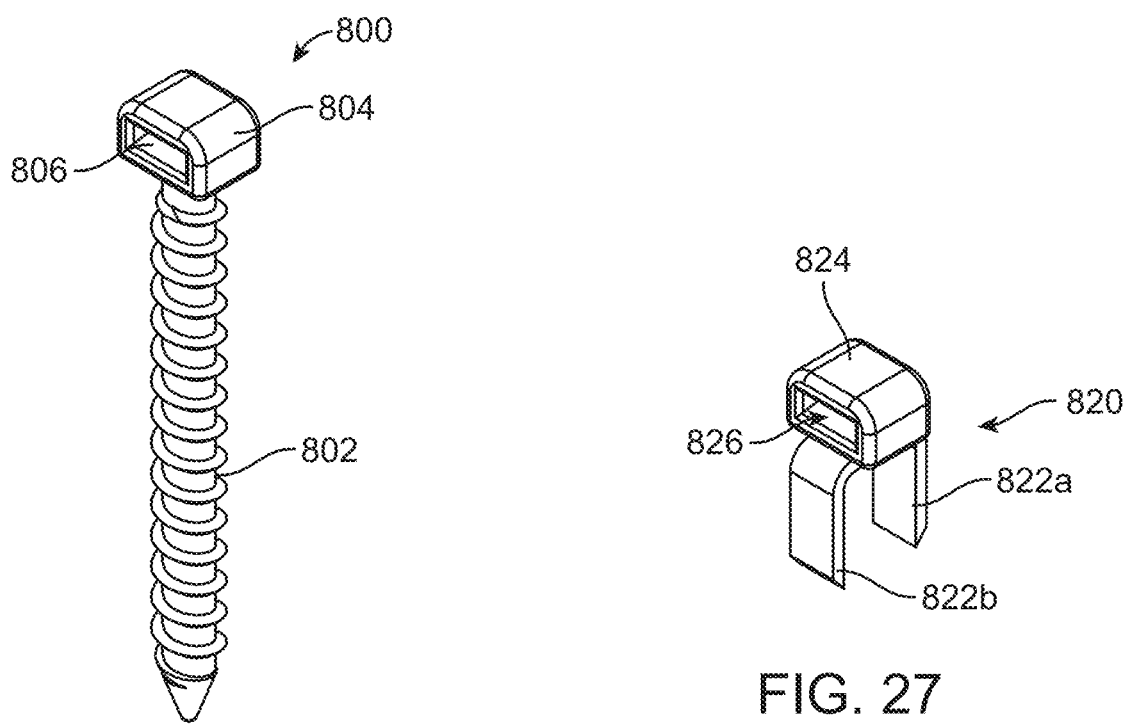
FIG. 26
FIG. 27
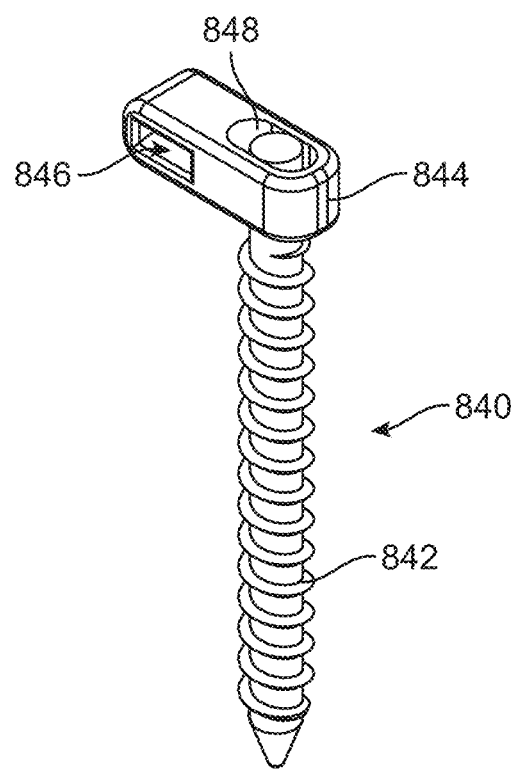
FIG. 28

SPINAL CURVATURE MODULATION SYSTEMS AND METHODS

RELATED APPLICATION DATA

This application is a continuation-in-part of U.S. Non-provisional patent application Ser. No. 16/302,733, filed on Nov. 19, 2018, which application was a 371 of international application No. PCT/US17/33592, filed on May 19, 20217, and claimed priority to U.S. Provisional Patent Application No. 62/338,763, filed on May 19, 2016. Each of these applications is incorporated by referenced herein in its entirety.

FIELD OF THE INVENTION

The present disclosure relates generally to orthopedic devices and methods for correcting or modulating spinal deformities utilizing non-fusion surgical treatments. More specifically, the disclosure relates to a non-fusion scoliosis construct which incorporates a flexible tether whose tension can be adjusted by a remotely controlled internal engine or by other mechanical means in a non-invasive manner. This facilitates the maintenance of corrective forces on the curvature of the spine without significant invasive surgical intervention.

BACKGROUND

Scoliosis is generally a term used to describe an abnormal curvature of the spine, usually in the thoracic or thoracolumbar region. Scoliosis is commonly broken up into different treatment groups, Adolescent Idiopathic Scoliosis, Early Onset Scoliosis and Adult (degenerative) Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebra and the bottom of the bottom vertebra. The term "idiopathic" means that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies with pedicle screws, in a manner that allows the spine to be straightened. Usually, at the section desired for fusion, the intervertebral disks are removed and bone graft material is placed to create the fusion. Alternatively, the fusion surgery may be performed anteriorly. A lateral and anterior incision is made for access. Usually, one of the lungs is deflated in order to allow access to the spine from this anterior approach.

In a less-invasive version of the anterior procedure, instead of the single long incision, approximately five incisions, each about three to four cm long are made in several of the intercostal spaces (between the ribs) on one side of the patient. In one version of this minimally-invasive surgery, rods and bone screws are placed and are secured to the vertebrae on the anterior convex portion of the curve. Once the patient reaches spinal maturity, it is difficult to remove the rods and associated hardware in a subsequent surgery, because the fusion of the vertebrae usually incorporates the rods themselves. Standard practice is to leave this implant in for life. With either of these two surgical methods, after fusion, the patient's spine is now relatively straight, but depending on how many vertebrae were fused, there are often limitations in the degree of flexibility, both in bending and twisting. As these fused patients mature, the fused section can impart large stresses on the adjacent non-fused vertebrae, and often, other problems including pain can occur in these areas, sometimes necessitating further surgery. This tends to be in the lumbar portion of the spine that is prone to problems in aging patients. Many physicians are now interested in non-fusion surgery for scoliosis, which may eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition occurring in only about one or two out of 10,000 children, but can be severe, sometimes affecting the normal development of organs. Because of the fact that the spines of these children will still grow a large amount after treatment, non-fusion distraction devices known as growing rods have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a high preponderance of infection.

In AIS patients, the treatment methodology for those with a Cobb angle between 20° and 40° is controversial. Many physicians prescribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. The patient compliance with brace wearing has been so problematic that there have been special braces constructed which sense the body of the patient, and keep track of the amount of time per day that the brace is worn. Coupled with the inconsistent patient compliance with brace usage, is a feeling by many physicians that braces, even if used properly, are not at all effective in treating scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment up until skeletal maturity.

In the treatment of patients with AIS, surgeons are leaning more towards non-fusion approaches using rigid growing rods. The growth of the rod is configured to be consistent with the normal growth pattern of the adolescent patient and the length of the rod is modulated by a magnetic system via an external magnetic driver in a non-invasive manner. Some surgeons are now beginning to use flexible tethers instead of rigid rods. In this method, a tether is applied on the convex side of the scoliosis curve using pedicle screws applied posteriorly or laterally onto each vertebra. The tether is appropriately tensioned to correct the curvature intraoperatively. As the patient grows, the tension in the tether is adjusted periodically (usually every 6 months) via a surgical approach. This procedure requires periodic re-operation subjecting the patient to an extended recovery period. Therefore, there is a need for spinal construct utilizing flexible tethers with an ability to modulate the tension of the tether form outside the body in a non-invasive manner.

Another problem with existing systems, even those employing flexible tethers, is that the tensioning devices and bone anchors could be difficult for the surgeon to configure and secure to the flexible tether. This can increase surgical procedure time and delay adoption of otherwise improved treatment devices and techniques. Additionally, given the forces sometimes required to be applied to the spine by the tether it may be difficult to maintain sufficient tether tensile strength without sacrificing flexibility. There thus remains a need in the art for further improvements in many aspects of available spinal curve modulation systems.

SUMMARY OF THE DISCLOSURE

In one implementation, the present disclosure is directed to a spinal curve modulation system for treating spinal curvature along a treatment region of the spine. The system includes a flexible tether of sufficient length to extend across the treatment region of the spine including across at least three adjacent vertebral bodies in a cranial-caudal direction; at least one first bone anchor configured to be fixed to a first vertebra and to the flexible tether; a tether tensioning unit comprising a tether interface member rotatable around a rotation axis and a remotely operable rotary drive operatively linked to the tether interface member to adjust tension in the flexible tether, said tension applied to the flexible tether in a direction perpendicular to the rotation axis; and at least one second bone anchor having a longitudinal axis perpendicular to the rotation axis and configured to fix the tether tensioning unit to a vertebra across the treatment region from at said at least one first bone anchor; wherein said tether tensioning unit is actuatable to adjust tension in the flexible tether without surgically exposing the flexible tether, said at least one first bone anchor or said at least one second bone anchor.

Other disclosed embodiments include bone anchors for securing a flexible tether to exert force on a bone. Such bone anchors comprise a threaded body portion with a tip configured to be screwed into bone and a head portion disposed on the threaded body portion opposite the tip, with the head comprising means for securing the flexible tether. Embodiments of means for securing the flexible tether include a threaded top formed on the head portion with an open window defined in the head portion under the threaded top for passing the tether therethrough, an upwardly open slot extending across the head portion transverse to the open window with a tether pin configured to be received in the upwardly open slot extending across the open window, and a tether pin cap with an internal thread configured to engage said threaded top and retain the tether pin in the upwardly open slot. Other embodiments of means for securing the flexible tether comprise two opposed side walls formed in the head portion defining an open slot therebetween and a tether pin extending across the open slot between the opposed side wall. The tether pin may be removable in such embodiments and may be secured by means such as recesses with detents, recesses or openings receiving an interference member such as a gasket or by internal threads.

In another implementation, the present disclosure is directed to a method of treating an abnormal spinal curvature along a treatment region of the spine. The method includes providing surgical access to the treatment region of the spine, the treatment region extending along the spine in a generally cranial-caudal direction and spanning at least three adjacent vertebrae; fixing a first bone anchor on a selected vertebra at a first end of the treatment region; fixing a second bone anchor having a longitudinal axis on a selected second vertebra spaced across the treatment region from the first bone anchor; fixing at least one third bone anchor on a selected vertebra between the first and second bone anchors; attaching a tether tension adjustment mechanism to the second bone anchor after fixing the second bone anchor to the selected second vertebra; extending a flexible tether between said tension adjustment mechanism and the first bone anchor; fixing the flexible tether to the at least one third bone anchor; manipulating said tension adjustment mechanism to initially tension the flexible tether so as to reposition vertebrae across the treatment region; closing the surgical access to the treatment region of the spine; and post-operatively, subsequent to closing the surgical access and without reopening or creating new surgical access to the flexible tether or bone anchors, manipulating said tension adjustment mechanism in vivo to periodically adjust tension in the flexible tether.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 24A is a perspective view of an anchor screw for a spinal curvature modulation system.

FIG. 24B is a front view of the anchor screw shown in FIG. 24A.

FIG. 24C is a detailed view of the anchor screw shown in FIG. 24B.

FIG. 25A is a perspective view of an alternate anchor screw for a spinal curvature modulation system.

FIG. 25B is a front view of the anchor screw shown in FIG. 25A.

FIG. 25C is a sectional view of the anchor screw shown in FIG. 25B through line A-A.

FIG. 25D is a detailed view of the anchor screw shown in FIG. 25C in an unlocked position.

FIG. 25E is a detailed view of the anchor screw shown in FIG. 25C in a locked position.

FIG. 26 is a perspective view of a slip screw for a spinal curvature modulation system.

FIG. 27 is a perspective view of a slip staple for a spinal curvature modulation system.

FIG. 28 is a perspective view of an alternate slip screw for a spinal curvature modulation system.

DETAILED DESCRIPTION

Embodiments described herein are directed to spinal curvature modulation systems, methods and related devices and instrumentation. In general and as described in greater detail below, embodiments of described systems include a flexible tether, a tether tensioning unit and bone anchors for the flexible tether that allow the tether to be secured across multiple vertebrae in a region of treatment. Tension in the flexible tether is adjustable transcutaneously with remote devices or with an elongate tool requiring only a small access incision, typically about 2 cm or less. Embodiments described thus allow for multiple adjustments of tether tension, and spinal curvature, over time without repeated, highly invasive, spinal surgeries.

Figure 1A:
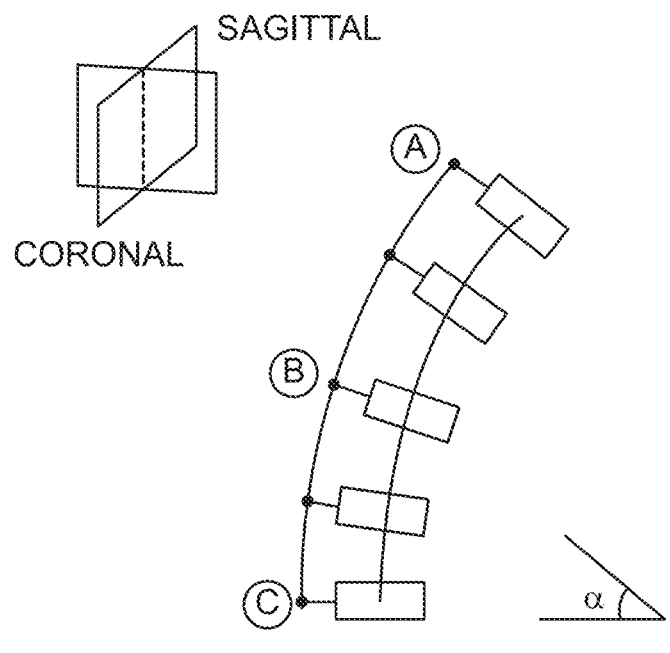
FIGS. 1A-D are illustrations of a spine from a posterior view with a tether attached laterally.
Figure 1B:
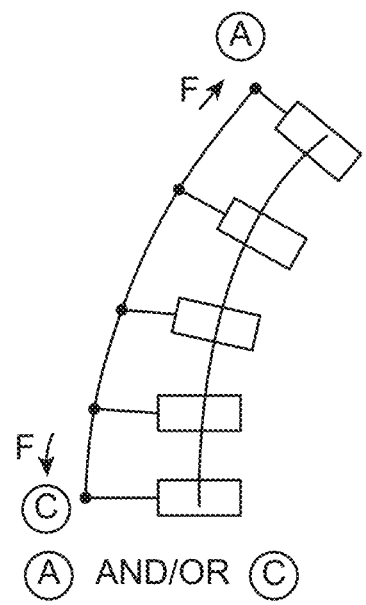
Figure 1C:
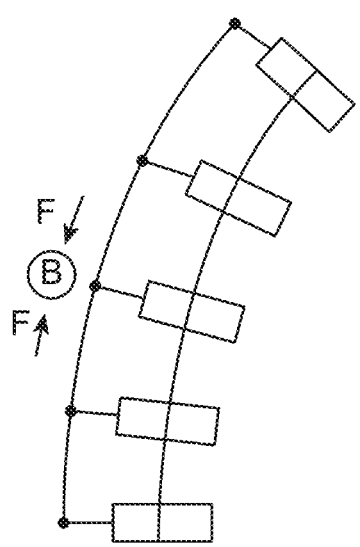
Figure 1D:
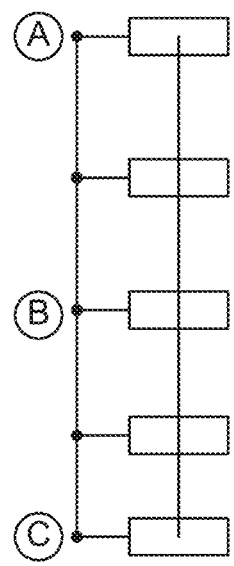

FIG. 1A shows a spine with a given angular deformity with angle alpha. With a lateral approach, screws can be placed into the vertebrae on the convex side of the curve, above and below the apex. Threaded through the screws is a flexible tether. This tether is fixed at the topmost and bottommost instrumented vertebrae across a region of treatment, but if there are any intermediate instrumented vertebrae, the tether is allowed to slide in eyes formed at the screw heads. How many vertebrae are instrumented is determined clinically but must be greater than or equal to 2. FIG. 1B shows a tensile force applied to the tether at location (A) and location (C) to correct the deformity. It is not necessary for the tensile force to be applied at both locations. Tensile force at location (A) and/or location (C) will correct the deformity. FIG. 1C shows an equal and opposite tensile force applied to the tether at location (B) to correct the deformity. FIG. 1D shows the same spine after tension force is applied at location (A), (B) and/or (C). The angular deformity has been corrected.

Figure 2A:
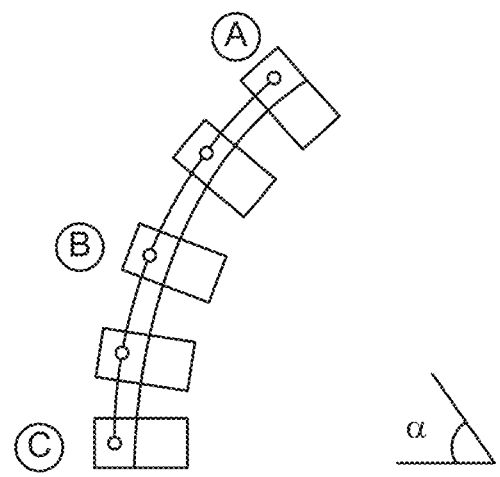
FIGS. 2A-D are illustrations of a spine from a posterior view with a tether attached posteriorly.
Figure 2B:
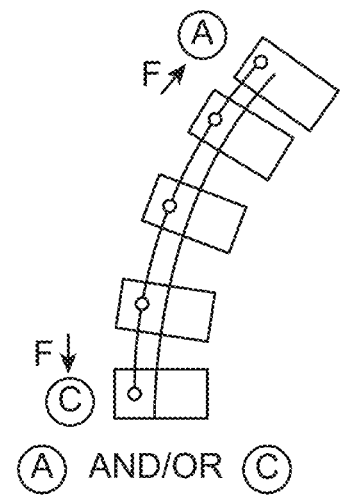
Figure 2C:
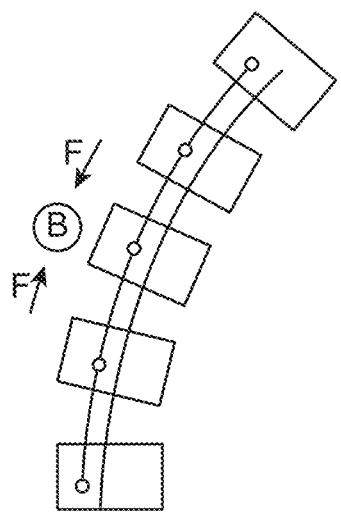
Figure 2D:
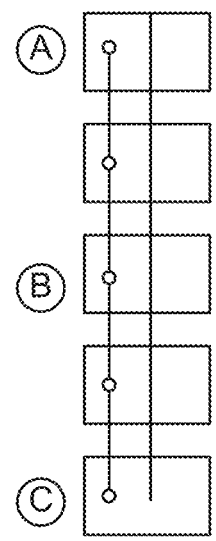

FIG. 2A shows a spine with a given angular deformity with angle alpha. With a posterior approach, pedicle screws can be placed into the vertebrae on the convex side of the curve, above and below the apex. Threaded through the pedicle screws is a flexible tether. This tether is fixed at the topmost and bottommost instrumented vertebrae, but if there are any intermediate instrumented vertebrae, the tether is again allowed to slide in the screw heads. How many vertebrae are instrumented is determined clinically but must be greater than or equal to 2. FIG. 2B shows a tensile force applied to the tether at location (A) and location (C) to correct the deformity. It is not necessary for the tensile force to be applied at both locations. Tensile force at location (A) and/or location (C) will correct the deformity. FIG. 2C shows an equal and opposite tensile force applied to the tether at location (B) to correct the deformity. FIG. 2D shows the same spine after tension force is applied at location (A), (B) and/or (C). The angular deformity has been corrected.

Figure 3:
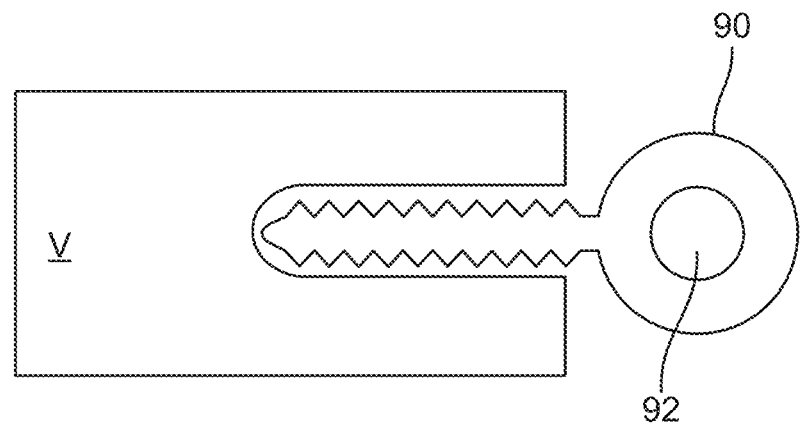
FIG. 3 is an illustration of a vertebra from a posterior view with a tether screw attached laterally.

FIG. 3 shows a screw 90 implanted into a vertebra (V). This screw is designed such that the tether may be threaded through eye 92 in the screw head such that the tether is constrained, but may still slide. Screw 90 also may be used to fix the free end of the tether to a vertebra by passing the tether through the eye and fastening it back to itself such as with a crimpable ferrule or other cable fixation device. A socket for a driving tool may also be provided on the outer end of the screw head.

Figures 4, 5:
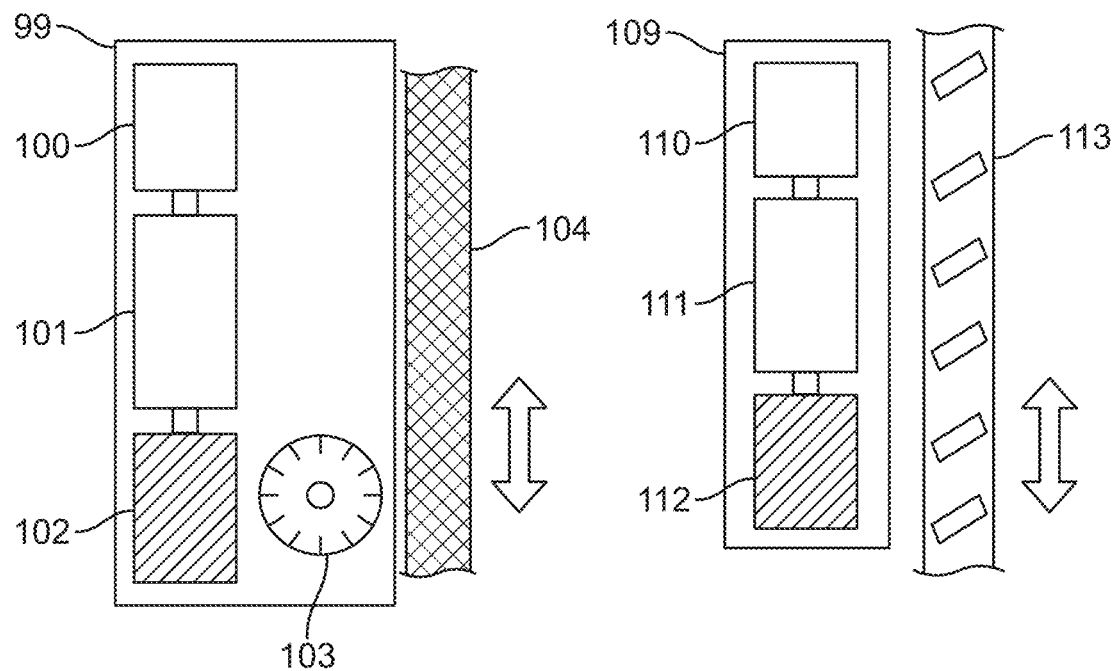
FIG. 4 is an illustration of an exemplary embodiment of a spinal curvature modulation system.
FIG. 5 is an illustration of an alternate embodiment of a spinal curvature modulation system.
Figure 32A:
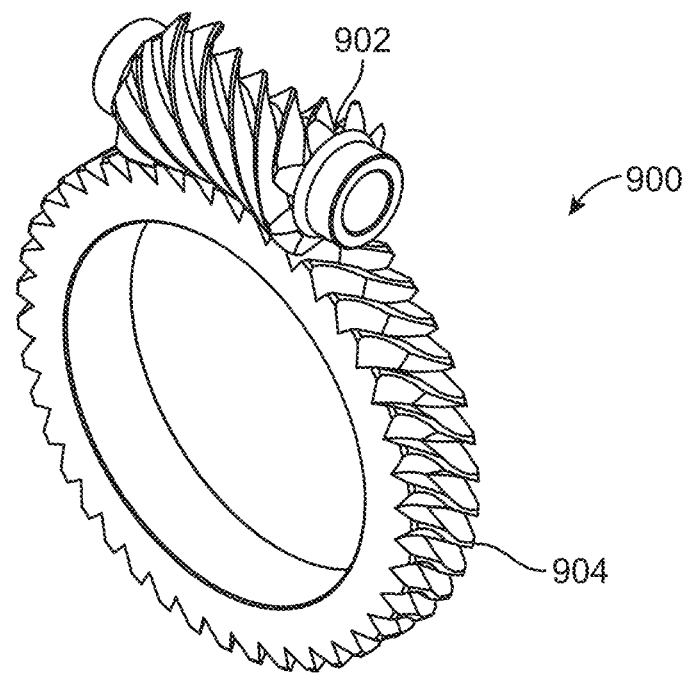
FIG. 32A is a perspective view of a globoid worm and spur gear mechanism.
Figure 32B:
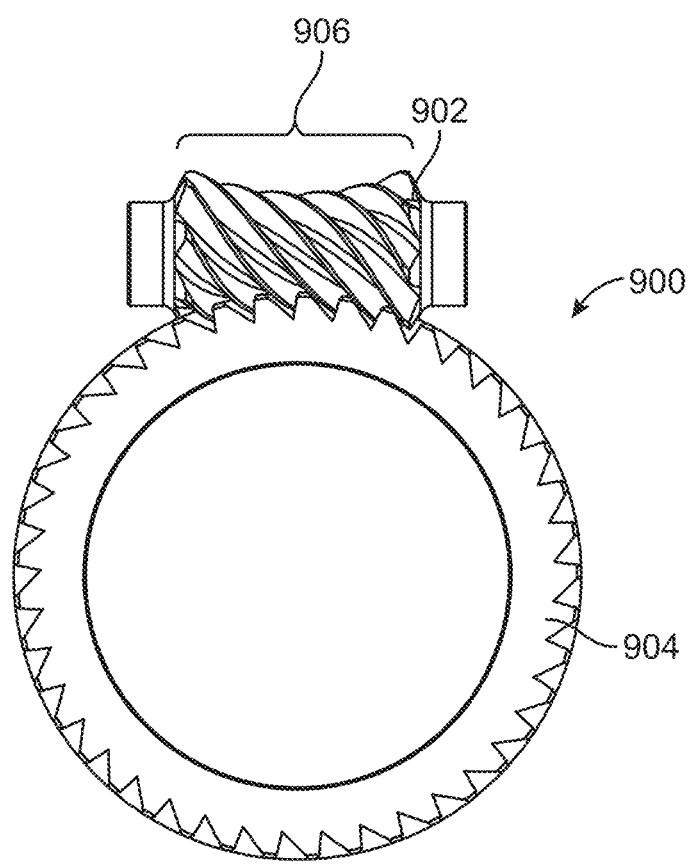
FIG. 32B is a side view of the globoid worm and spur gear mechanism shown in FIG. 32A.

FIG. 4 schematically illustrates an embodiment of a spinal curvature modulation system. The system includes a tether tensioning unit 99, which in this example comprises a transcutaneously actuatable drive mechanism including an internal actuator 100 acting through gearbox 101 to drive worm gear 102 and tether interface 103. The worm gear in turn drives tether interface 103 to tension or de-tension flexible tether 104. In one example, internal actuator 100 may comprise a magnetic motor with a remotely controllable rotatable magnet, which can be driven by an external driver mechanism (see, e.g. FIG. 15). The external driver mechanism may comprise another rotatable magnet and a mechanism for controlling the rotation of that magnet, for example an electric motor and control system. An exemplary gear set for gearbox 101 is shown in FIGS. 32A and 32B. In one example, rotation of worm gear 102 rotates a tether interface 103 through engagement with meshing spur gear teeth. In one alternative the teeth of the spur gear may directly engage the flexible tether to form tether interface 103 such that when the spur gear rotates it provides a force on the tether 104 to either increase or decrease the tension in the tether 104. In an alternative embodiment, a separate tether engaging member is combined with the spur gear, for example integrally side by side or disposed on a common shaft, to form tether interface 103. In such an alternative embodiment, the tether engaging member may be formed as a wheel, disk or other rotatable member with a periphery configured to mesh with the material of the flexible tether, such as teeth, spikes, abrasive or other high friction surface. In one example, tether 104 may be formed as a cable, band or ribbon made from a braided polymer or metal, for example ultra-high molecular weight polyethylene (UHMWPE), polyethylene terephthalate (PET), thermoplastic polycarbonate polyurethane (PCU, e.g., Bionate®) or a multilayered polymeric strand comprising low molecular and high molecular weight polyethylene. Metals employed may comprise stainless steel, titanium and alloys thereof in solid or braided configurations. The tether 104 may be designed with a tensile strength higher than 300N. When the tether 104 is attached to multiple vertebrae it can be used to correct spinal deformities as described herein. Flexibility of tether 104 should be at least sufficient to conform to the existing curvature of the area of the spine to be treated without experiencing plastic deformation, in other words, sufficient to maintain resiliency in all modes of operation.

It is to be understood that the embodiments disclosed herein are disclosed as exemplary embodiments to illustrate, when considered as a disclosure as a whole, the various features, components and steps of embodiments of the present invention. Each combination of components as would be understood by persons of ordinary skill in the art based on the teachings herein is not explicitly shown because all possible combinations will be appreciated and understood from the embodiments illustrated. For example, it will be understood that unless otherwise described any disclosed internal actuator, gearbox and drive gear disclosed may be used in any combination to make up a tether tensioning unit in accordance with the teachings of the present disclosure. Similarly, any compatible combination of disclosed tether interface and flexible tether may be used together with any disclosed tether tensioning unit. Thus, it will be understood, for example, that tether tensioning unit 99, while illustrated above as employing a magnetically actuated internal actuator 100, may also employ any other internal actuator within the scope of the present disclosure.

FIG. 5 schematically illustrates another embodiment of a spinal curvature modulation system utilizing a flexible band tether in which tension is controlled by tether tensioning unit 109. In this exemplary embodiment, the system includes a rotatable magnet 110 as an internal actuator, which can be driven by an external driver mechanism (see, e.g., FIG. 15). The rotation of the magnet 110 drives a gearbox 111 which in turn drives a worm gear 112; the worm gear acting as the tether interface. The teeth of the worm gear 112 mesh with diagonal cuts in a band tether 113. Rotation of the worm gear 112 provides a force on the band tether 113 to either increase or decrease the tension in the band tether 113. When the band tether 113 is attached to multiple vertebrae, it can be used to correct spinal deformities.

Figure 6:
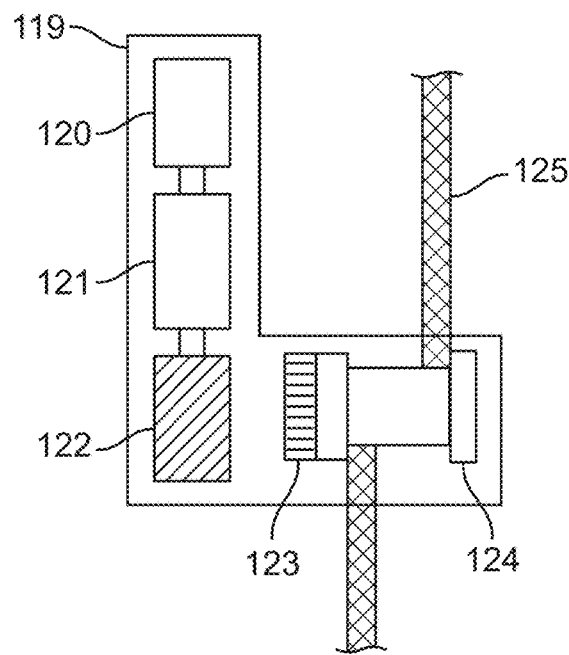
FIG. 6 is an illustration of an alternate embodiment of a spinal curvature modulation system.

FIG. 6 schematically illustrates a further embodiment of a spinal curvature modulation system in which flexible tether tension is controlled by tether tensioning unit 119. The system includes an electric motor 120 as internal actuator which can be driven by an externally induced current or via subcutaneous power leads (see, e.g., FIG. 10). A suitable electric motor for this purpose may be one that provides power in the range of about 1.0-1.2 W. Alternatively, electric motor 120 may be replaced with a magnetic drive or other internal actuator as described herein. The rotation of the motor 120 drives a gearbox 121 which in turn drives a worm gear 122. Rotation of the worm gear 122 rotates the tether interface, in this example a spur gear 123 attached to or integral with spool 124 such that they rotate together. When the spool 124 rotates it provides a force on the tether 125 to either increase or decrease the tension in the tether 125. When the tether 125 is attached to multiple vertebrae, it can be used to correct spinal deformities.

Figure 7:
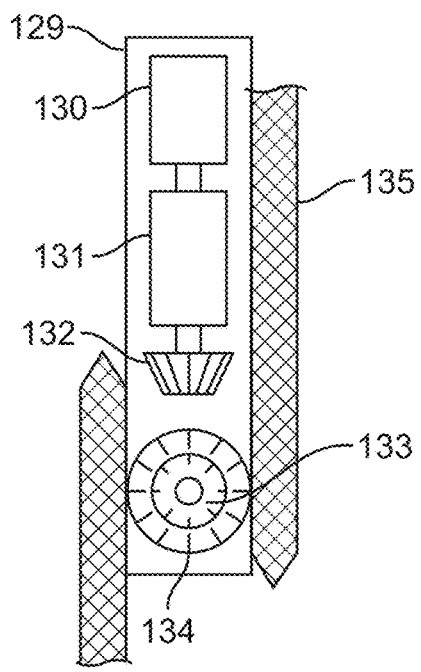
FIG. 7 is an illustration of an alternate embodiment of a spinal curvature modulation system.

FIG. 7 schematically illustrates another embodiment of a spinal curvature modulation system in which flexible tether tension is controlled by tether tensioning unit 129. The system includes internal actuator 130 as described in other embodiments which can be driven by, for example, an external driver mechanism (see, e.g. FIG. 15) or induction or directly delivered current (see, e.g., FIG. 10). Alternatively, a manual drive may be used. The rotation of the internal actuator 130 drives a gearbox 131 which in turn drives a bevel gear 132. Rotation of the bevel gear 132 rotates the tether interface comprising, in this example, a second bevel gear 133 and spur gear 134, which may be attached or integrally formed. Bevel gear 133 is perpendicular from the first bevel gear 132 and spur gear 134 is attached to the second bevel gear 133 such that they rotate together. The teeth of the spur gear 134 mesh with two flexible tethers 135 which continue in opposite directions. When the spur gear 134 rotates it provides equal and opposite forces on the two tethers 135 to either increase or decrease the tension in the tethers 135. When the tethers 135 are attached to multiple vertebrae, it can be used to correct spinal deformities.

Figure 8:
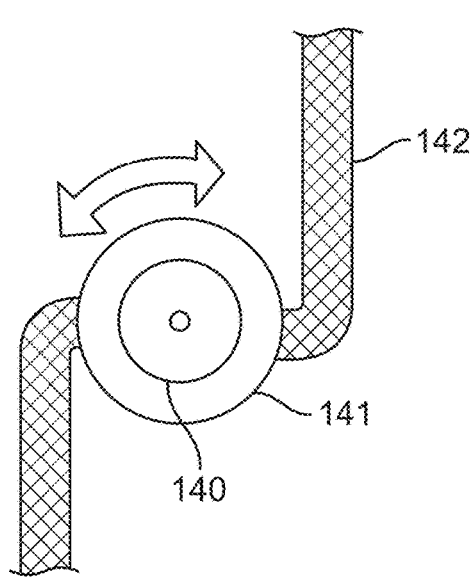
FIG. 8 is an illustration of an alternate embodiment of a spinal curvature modulation system.

FIG. 8 schematically illustrates a detail of an alternative embodiment of a spinal curvature modulation system. In this example, the system includes a rotatable magnet 140 as internal actuator, which can be driven by an external driver mechanism (see, e.g. FIG. 15). The magnet 140 is attached to a housing 141 such that they rotate together. The housing is attached to two tethers 142 such that when the housing 141 rotates, it provides equal and opposite forces on the two tethers 142 to either increase or decrease the tension in the tethers 142. When the tethers 142 are attached to multiple vertebrae, it can be used to correct spinal deformities.

Figure 9:
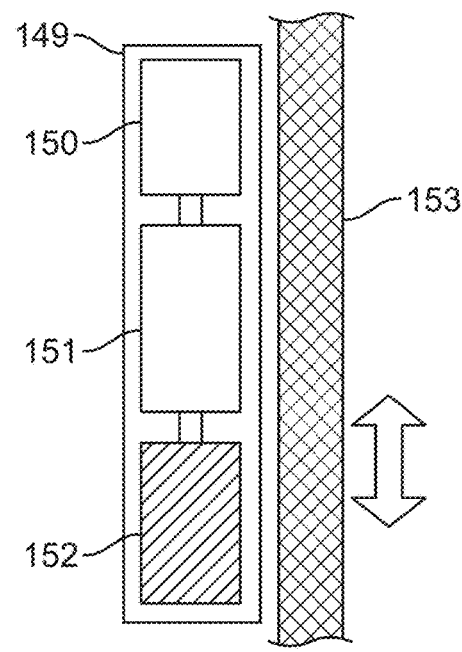
FIG. 9 is an illustration of an alternate embodiment of a spinal curvature modulation system.

FIG. 9 schematically illustrates another exemplary embodiment of a spinal curvature modulation system in which flexible tension is controlled by tether tensioning unit 149. The system includes a rotatable magnet 150 as internal actuator, which can be driven by an external driver mechanism (see, e.g., FIG. 15). Once again, as elsewhere described herein, other disclosed internal actuators may be substituted for the magnetic drive. The rotation of the magnet 150 drives a gearbox 151 which in turn drives tether interface 152, in this case formed as a threaded cylinder or other axially rotatable member. As tether interface 152 rotates, the threads of the threaded portion (referenced by a plane coincident with the axis of rotation) translate up or down. The threads of tether interface 152 thus mesh with a flexible tether 153 such that rotation provides a force on the tether 153 to either increase or decrease the tension in the tether 153. When the tether 153 is attached to multiple vertebrae, it can be used to correct spinal deformities.

Figure 10:
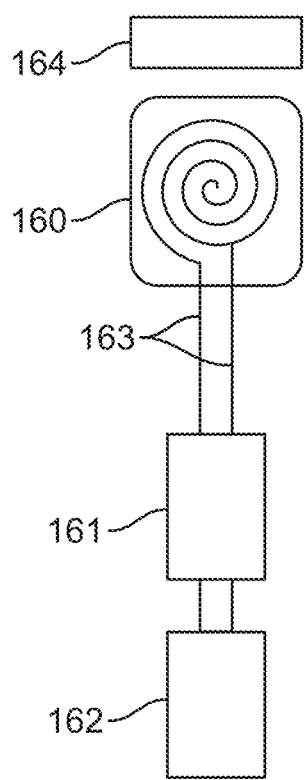
FIG. 10 is an illustration of an alternate embodiment of a spinal curvature modulation system.

FIG. 10 schematically illustrates an embodiment of a tether tensioning unit for a spinal curvature modulation system in which an electronic drive mechanism is provided. A wire coil 160 draws power from an externally positioned inductive wireless power transfer device 164 to feed an electric motor 161 to drive a gearbox 162, which in turn can be used in conjunction with mechanisms in the other embodiments described herein to apply a force on a tether to either increase or decrease the tension in the tether. Alternatively, or additionally, subcutaneous leads 163 may be provided, which can be easily accessed and direct power applied thereby. Examples of inductive wireless power transfer systems suitable for use in embodiments of the present invention are disclosed, for example, in U.S. Pat. No. 6,092,531 and U.S. Patent Publication No. 2010/0201315, which are incorporated by reference herein in their entirety.

Figure 11:
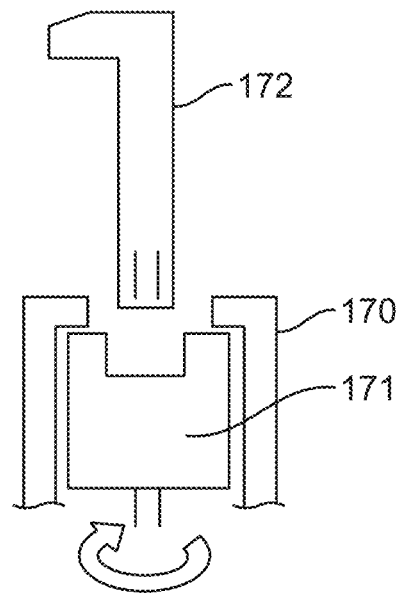
FIG. 11 is an illustration of an alternate embodiment of a spinal curvature modulation system.

FIG. 11 schematically illustrates a detail of another embodiment of a spinal curvature modulation system utilizing a manual, hand-driven drive mechanism. In this example, the internal actuator comprises housing 170, which holds a drive nut 171. Drive nut 171 can be accessed through a small incision and can be rotated with an elongate manual tool 172 configured to engage the internal actuator. The drive nut 171 can be used in conjunction with other internal actuators described herein to provide redundant drive mechanisms for applying a force on a tether to either increase or decrease the tension in the tether. As used herein, a small incision, to permit access of an elongate tool to actuate a manual drive internal actuator, is an incision generally between about 1-3 cm in length and more typically about 2 cm in length.

Figure 12:
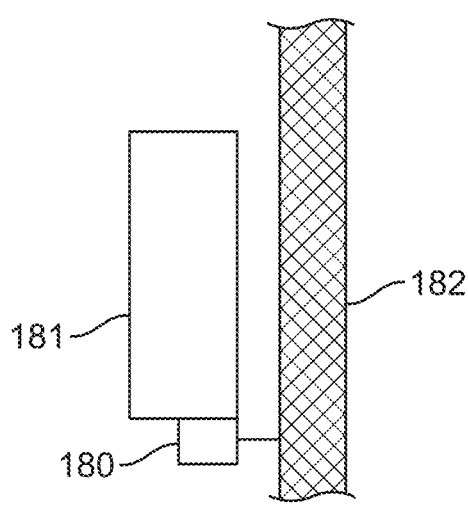
FIG. 12 is an illustration of an alternate embodiment of a spinal curvature modulation system.

FIG. 12 schematically illustrates a further alternative embodiment of a spinal curvature modulation system where a tether tension sensor 180 is integrated into the tether tensioning unit 181 to measure the tension applied to the tether 182. Sensor 180 may comprise a compatible tension sensing device, such as single roller or multi-roller sensors or direct strain gauge sensors, as may be selected by persons of ordinary skill in the art based on the teachings herein. Sensor 180 may be configured to directly sense tension in the flexible tether or it may be positioned to sense torque or force within tether tensioning unit as an indicator of tension in the flexible tether. Tether tensioning unit 181 may comprise any of the magnetic, electronic or manual drive mechanisms as disclosed herein, or other suitable mechanism as may be derived by a person of ordinary skill based on the teachings of the present disclosure.

Figure 13:
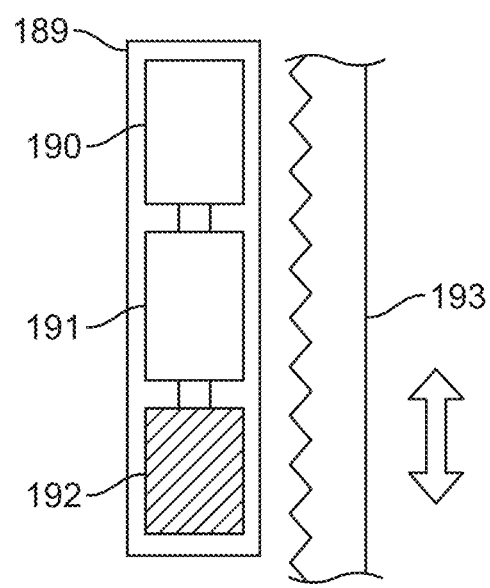
FIG. 13 is an illustration of an alternate embodiment of a spinal curvature modulation system.

FIG. 13 schematically illustrates another alternative embodiment of a spinal curvature modulation system in which flexible tether tension is controlled by tether tensioning unit 189. The system includes a rotatable magnet 190 as an internal actuator, which can be driven by an external driver mechanism (see, e.g., FIG. 15). The rotation of the magnet 190 drives a gearbox 191 which in turn drives the tether interface, in this example, formed as worm gear 192. The teeth of the worm gear 192 mesh with tooth-shaped cuts in a band tether 193. Rotation of the worm gear 192 provides a force on the band tether 193 to either increase or decrease the tension in the band tether 193. When the band tether 193 is attached to multiple vertebrae, it can be used to correct spinal deformities.

Figure 14:
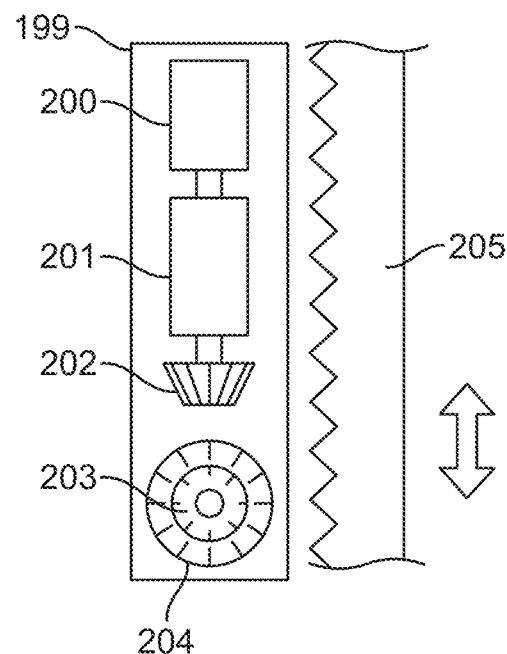
FIG. 14 is an illustration of an alternate embodiment of a spinal curvature modulation system.

FIG. 14 schematically illustrates an alternative embodiment of a spinal curvature modulation system in which flexible tether tension is controlled by tether tensioning unit 199. In this example, tether tensioning unit 199 includes a rotatable magnet drive 200 as elsewhere described, but may alternatively employ other internal actuators as also described. The rotation of the magnet 200 drives a gearbox 201 which in turn drives a bevel gear 202. Bevel gear 202 engages the tether interface comprising, in this example, a second bevel gear 203 and spur gear 204. Thus, rotation of the bevel gear 202 rotates second bevel gear 203 which is perpendicular from the first bevel gear 202. Spur gear 204 is attached to the second bevel gear 203 such that they rotate together. The teeth of the spur gear 204 mesh with diagonal cuts in a band tether 205. Rotation of the spur gear 204 provides a force on the band tether 205 to either increase or decrease the tension in the band tether 205. When the band tether 205 is attached to multiple vertebrae, it can be used to correct spinal deformities.

The use of a gear box 201 between the magnet 200 and the bevel gear 202 is highly advantageous for transferring the lower force of the rotating magnet to a much higher force required for tensioning the band tether 205 to correct deformities of the spine. In one particular embodiment the gear box 201, bevel gears 202 and 203, and spur gear 204 transfer 1000 rotations of the magnet 200 into 1 mm of translation of the tether band 205. In addition to transferring sufficient force for correcting deformities of the spine, the gear box 201 and related bevel gears 202 and 203 and spur gears 204 are also beneficial in resisting the forces the corrected spine will place on the system as it tries to resist the correction. The gear box 201, bevel gears 202 and 203 and spur gears 204 act as a lock preventing the tension in the tether band 205 from reversing rotation of the spinal curvature modulation system. A gearbox that reduces the rotations of the rotating magnet at a ratio of approximately 1000 to 1 is beneficial at resisting the forces from the spine. Depending on parameters such as the type and size of the internal actuator, gear reduction ratios in the range of about 300:1 to about 5000:1 may be utilized in the gearbox.

Figure 15:
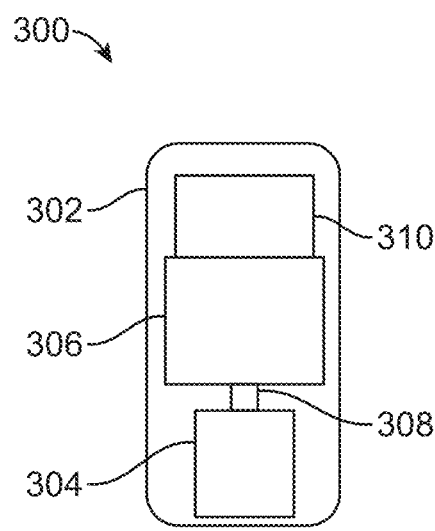
FIG. 15 is an illustration of a magnetic drive mechanism for adjusting a spinal curvature modulation system.

FIG. 15 schematically illustrates one exemplary embodiment of an external magnetic drive mechanism 300 as may be utilized with magnetically driven embodiments described herein. In this embodiment, housing 302 contains drive magnet 304 and motor 306 connected to drive magnet 304 via drive shaft 308. Controller 310 controls the operation of motor 306. Controller 310 may include a programmable processor or other control system to permit precise, preprogrammed control, as well as intra-procedural adjustments by the surgeon. Controller 310 may also include a sensor or other wireless communication device, for example, to receive tether tension information from a tension sensor such as sensor 180, shown in FIG. 12. Further details of suitable magnetic drive mechanisms are disclosed, for example, in U.S. Pat. Nos. 8,915,915 and 8,439,915, both of which are incorporated herein in their entirety.

Figure 16:
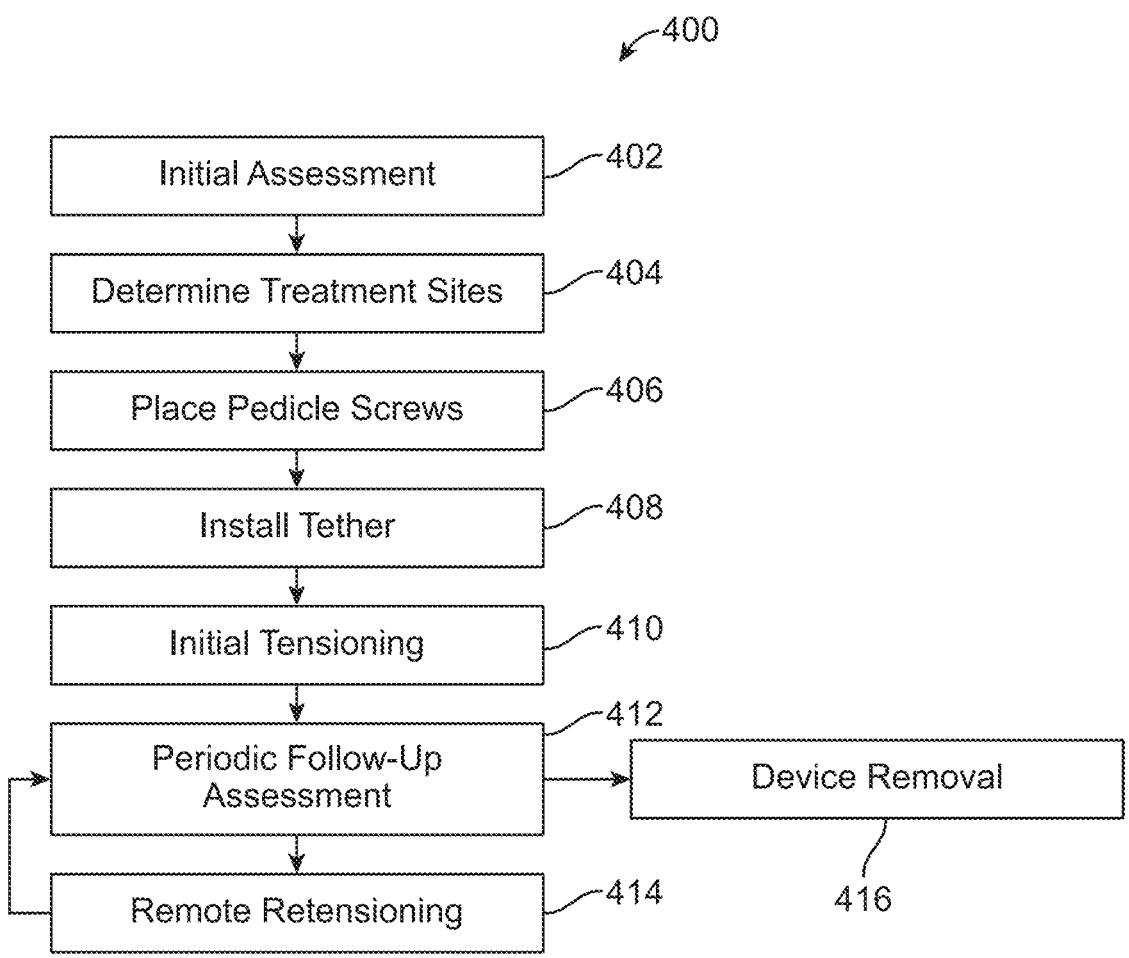
FIG. 16 is a flow chart illustration of a treatment method for spinal curvature modulation.

FIG. 16 is a flow chart illustrating one exemplary embodiment of a treatment method 400 according to the present disclosure. As shown in FIG. 16, after an initial patient assessment 402, a determination is made as to the region to be treated including the vertebrae to be treated and the number and location of pedicle screws to be placed 404. A surgical access is created to the treatment region and bone anchors, typically, pedicle screws or other suitable bone anchors, are then placed 406 as determined in the prior step in accordance with standard surgical procedures. Exemplary bone anchors are illustrated in FIGS. 3, 24A and 25A. After placement of the bone anchor is confirmed, one or more tethers are installed 408 corresponding to the treatment modality determined in the initial assessment. Installation of the tether typically comprises attachment of a tether-free end to a bone anchor at one end of the treatment region and attachment of the tether tensioning unit to a bone anchor at an opposite end of the treatment region. When dual acting or opposed tethers are employed, for example as shown in FIGS. 6-8, then the tether tensioning unit may be secured to a bone anchor in a mid-range of the treatment region and tethers secured to bone anchors at opposite ends of the treatment region. After installation of the tether(s), the tethers are initially tensioned 410. Initial tensioning may be accomplished before closure in order to confirm proper function. At periodic intervals after healing from the initial surgery to install the system, the patient is reassessed in follow-up assessments 412. An amount of additional movement is determined and corresponding additional or retensioning calculated based on the determined movement. Re-tensioning is remotely or manually effected 414 without creating a new surgical access to the tether or bone anchors using a drive mechanism appropriate for the installed system based on the follow-up assessment. Follow-up assessment and re-tensioning may be repeated as necessary until follow-up assessment indicates treatment is complete. Thereafter, the installed distraction system may be surgically removed 416.

Figure 17:
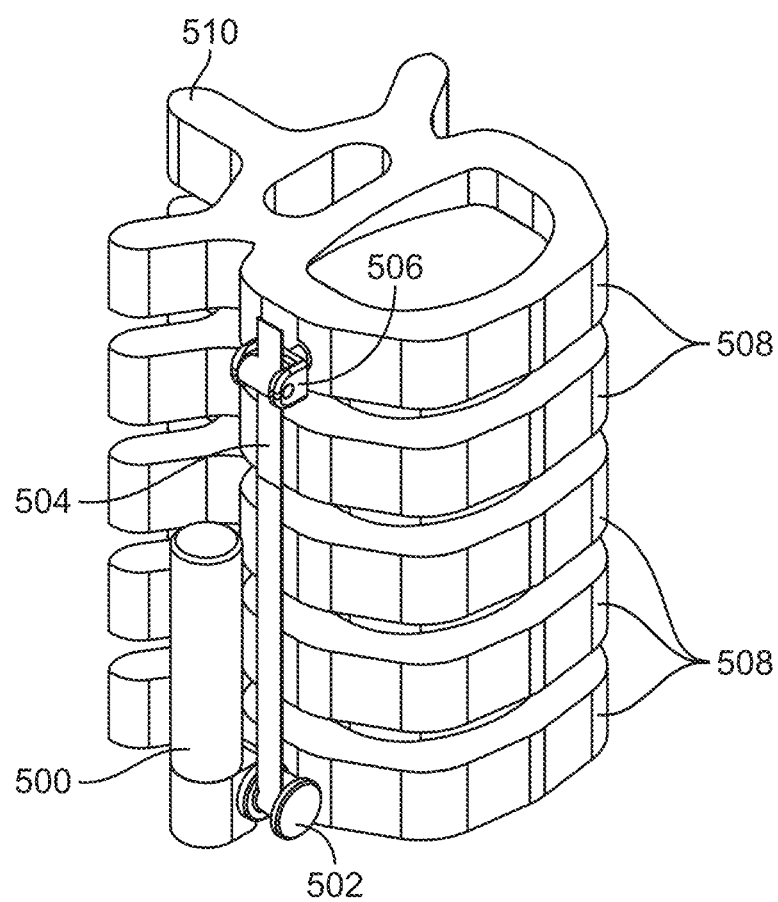
FIG. 17 is a perspective view of a further alternative embodiment of a spinal curvature modulation system according to the present disclosure.
Figure 17A:
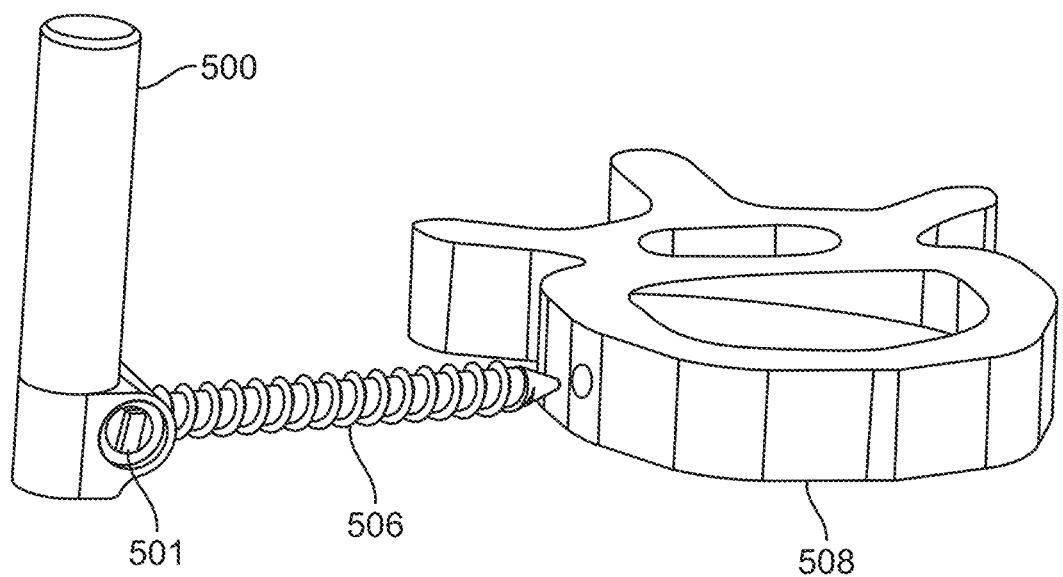
FIG. 17A is a perspective view of tether tensioning unit and bone anchor utilized to fix the tether tensioning unit to a vertebrae according to embodiments described herein.

FIG. 17 shows another exemplary spinal curvature modulation system attached laterally to a spine. The system comprises tether tensioning unit 500, flexible tether 504, a tether interface 502, in this case formed as a spool, and a tether bone anchor 506 attached to at least two vertebral bodies 508. One tether bone anchor 506 is attached to a vertebral body 508 at one end of the flexible tether 504 and tether tensioning unit 500 is attached to a vertebral body 508 at the other end of the flexible tether 504 with a second bone anchor as shown in FIG. 17A. The flexible tether 504 is wrapped around the tether spool 502 at one end and is fixed at the tether anchor 506 at the other end. The tension in the flexible tether 504 is increased or decreased by tether tensioning unit 500 by rotation of the tether spool 502 as was described above. Tether tensioning unit 500 can be positioned in any of a number of locations and still perform its function. Tether tensioning unit 500 can be comprised of any of the various elements described in the embodiments shown in FIGS. 4-14.

Figure 18:
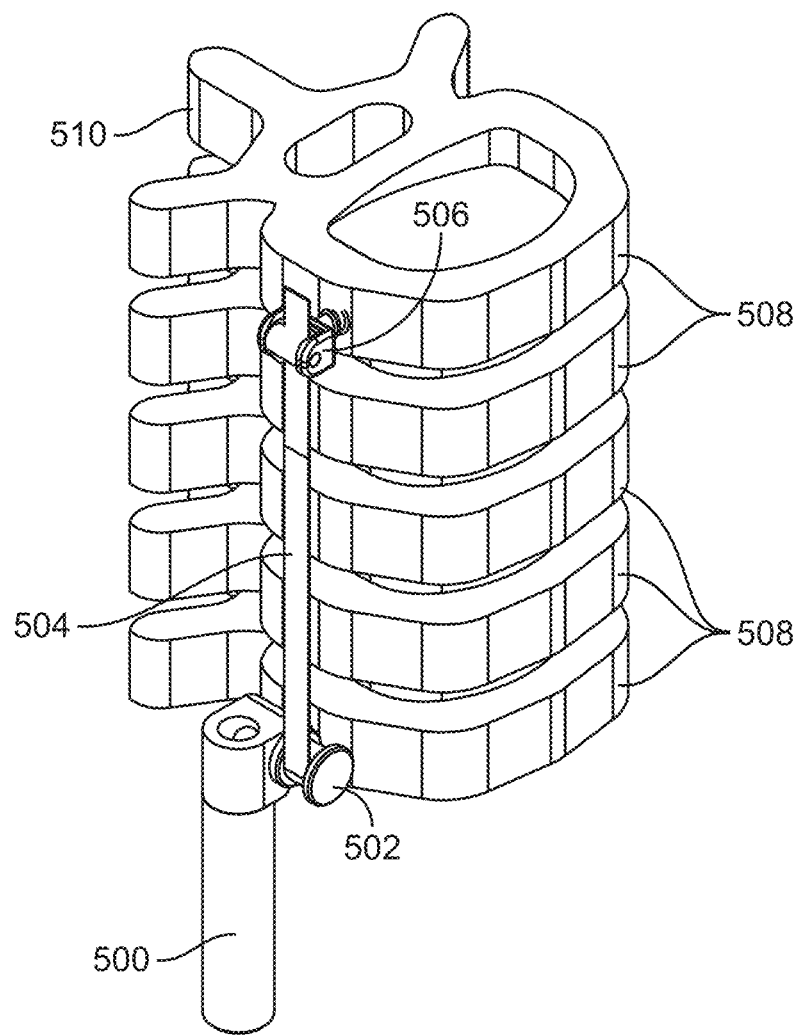
FIGS. 18, 19, 20, 21, 22, and 23A are perspective views of embodiments of spinal curvature modulation systems showing alternative positioning in accordance with the present disclosure.
Figure 19:
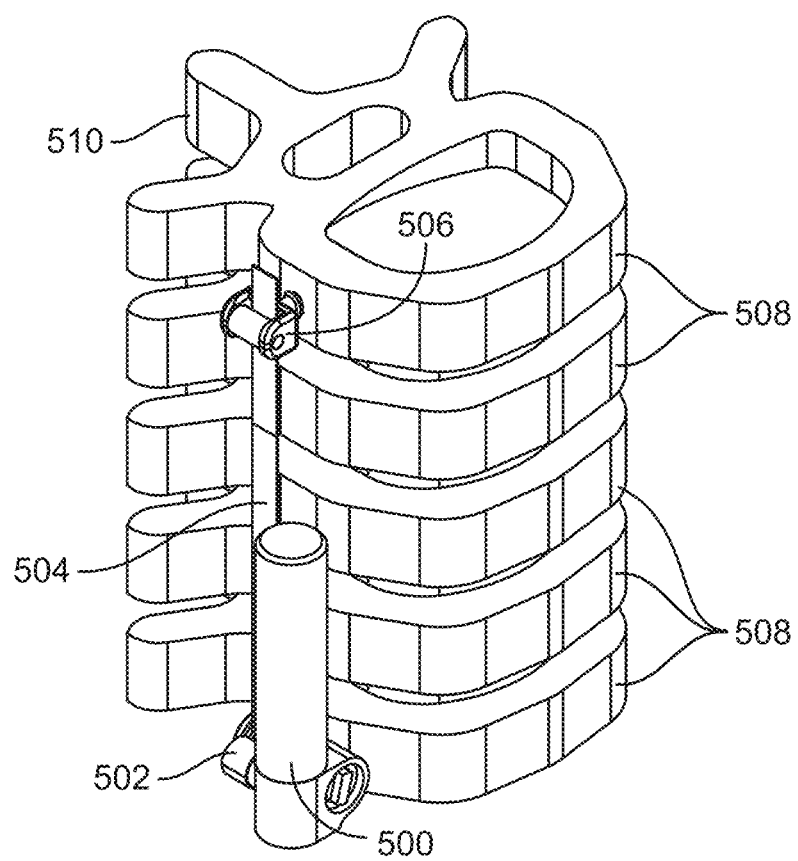
Figure 20:
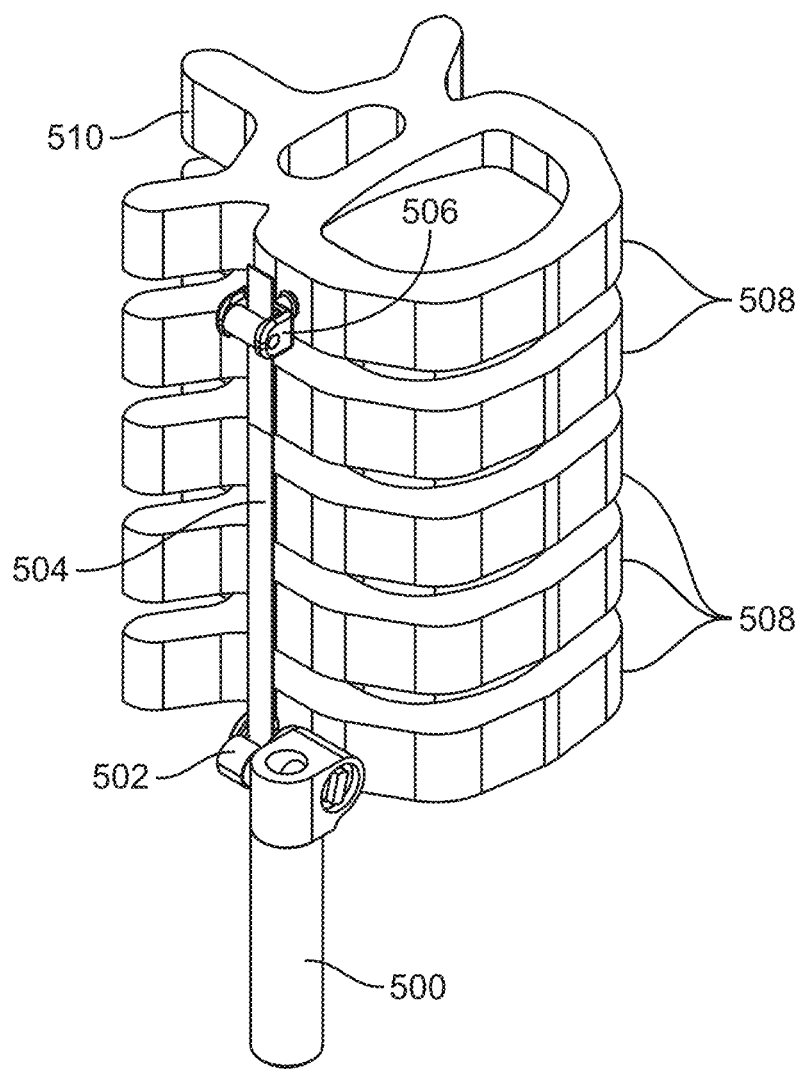
Figure 21:
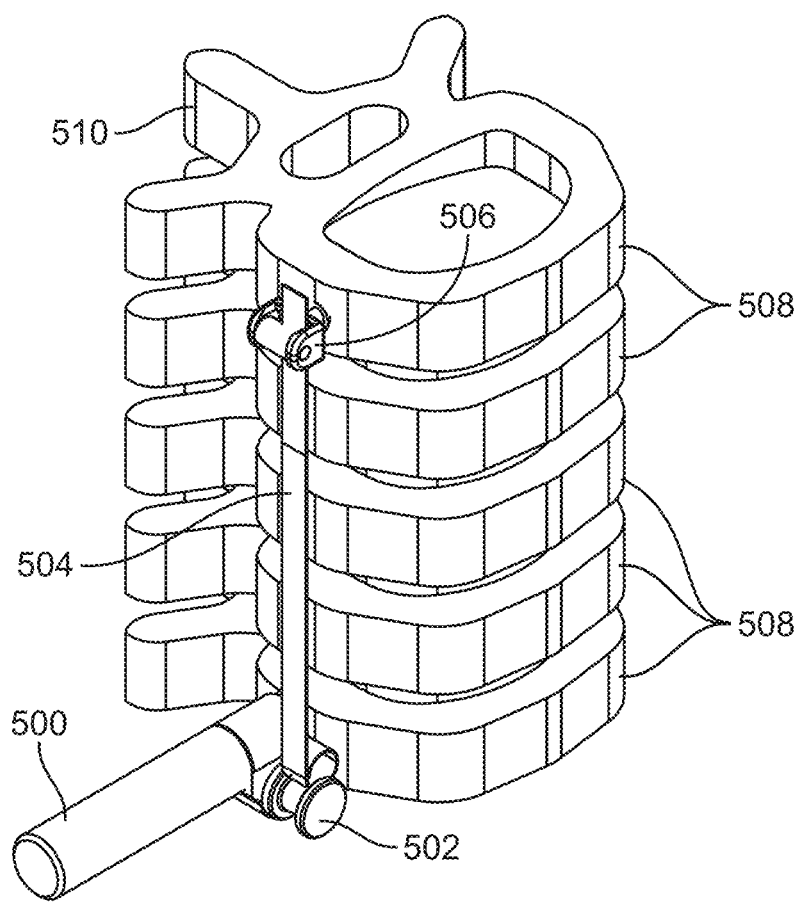
Figure 22:
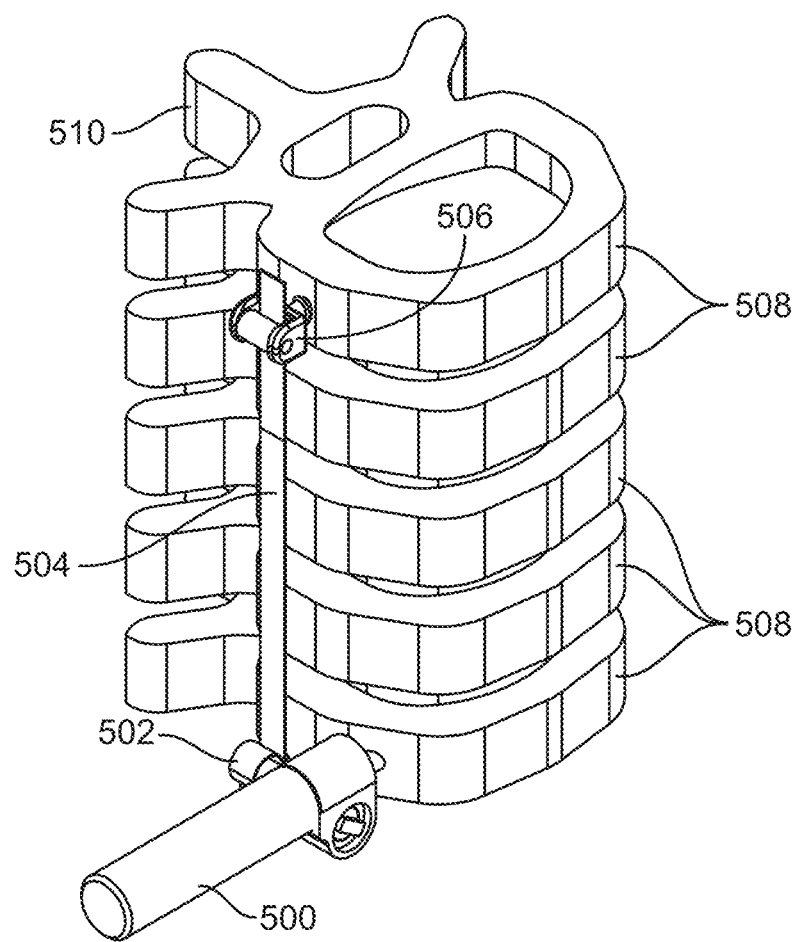
Figure 23A:
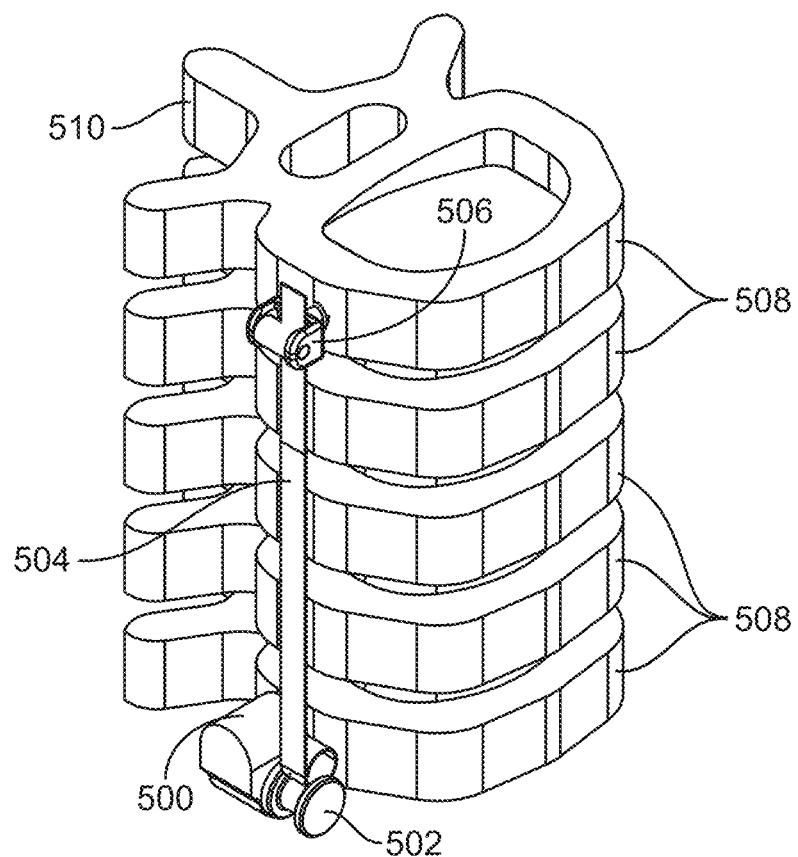
Figure 23B:
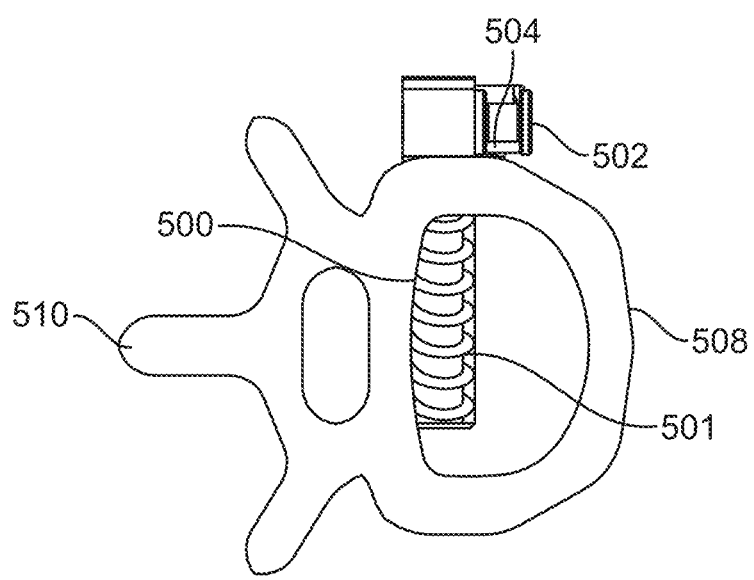
FIG. 23B is a cephalad view of an alternative embodiment of the spinal curvature modulation system shown in FIG. 23A.
Figure 23C:
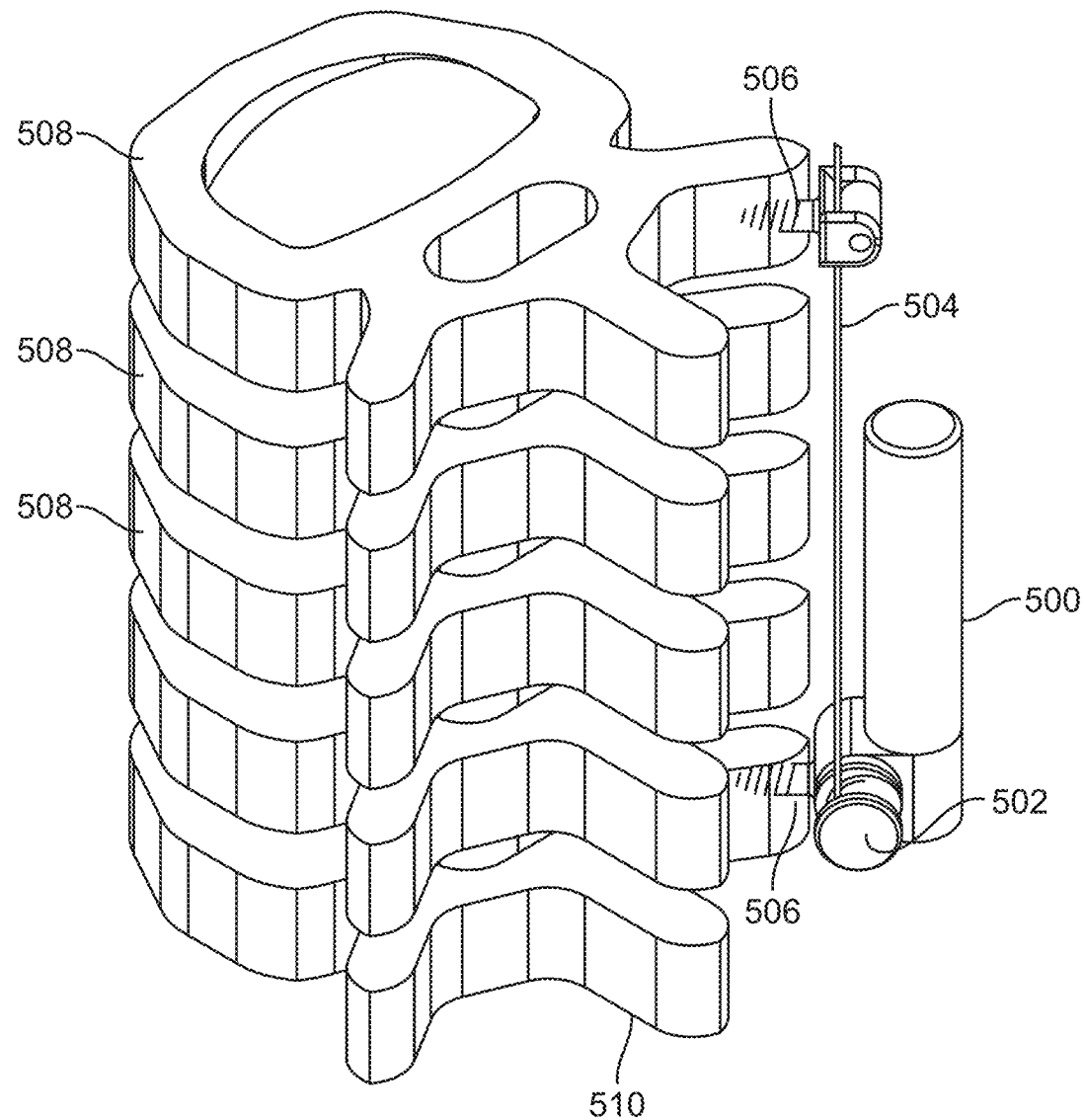
FIG. 23C illustrates posterior positioning of a spinal curvature modulation system according to embodiments described herein.

In FIG. 17, tether tensioning unit 500 is positioned posterior and superior in relationship to tether interface 502 as indicated by the spinous process 510 which is on the posterior of the spine. In FIG. 18 tether tensioning unit 500 is positioned posterior and inferior to tether interface 502 and flexible tether 504. In FIG. 19 tether tensioning unit 500 is positioned anterior and superior to tether interface 502. In FIG. 20 tether tensioning unit 500 is positioned anterior and inferior to tether interface 502 and flexible tether 504. In FIG. 21 tether tensioning unit 500 is positioned posterior and lateral to tether interface 502 and flexible tether 504. In FIG. 22 tether tensioning unit 500 is positioned anterior and lateral to tether interface 502 and flexible tether 504. In FIG. 23A tether tensioning unit 500 is positioned posterior and medial to tether interface 502 and flexible tether 504. The medial location can be better seen in FIG. 23B which shows a cutaway view of the vertebral body 508 revealing tether tensioning unit 500 inside the vertebral body 508. The tether tensioning unit may be attached to the vertebral body by a screw or staple extending from the mechanism as shown, for example in FIG. 17A. With the medial location, tether tensioning unit itself can have an external threaded profile 501 or extending staple arms for direct attachment to the vertebral body. Tether tensioning unit 500 can also be positioned anterior and medial to the flexible tether 504 (not shown). There are many reasons a surgeon may select different adjustment mechanism locations including but not limited to a) preservation of the normal motion of the adjacent spine segments above or below the spinal curvature modulation system, b) avoid impingement of any sensitive nearby anatomic member, or c) the desire to have a low profile implant that does not create any visible change to the patient's outside appearance. Although FIGS. 17-23C show tether tensioning unit 500 located at a caudal end of the treatment region or spine segment being treated, tether tensioning unit 500 can alternately be located at the cephalad end or in the middle of the treatment region as previously described and still be positioned in the various locations described relative to the flexible tether 504. With positioning in or proximate the middle of the treatment region, dual tether devices such as shown in FIGS. 6-8 may be employed.

FIGS. 18-23B also show the spinal curvature modulation system attached laterally to the vertebral bodies 508. As previously described, the spinal curvature modulation system can also be attached from the posterior side or posterior-lateral side to the vertebral bodies 508 as shown in FIG. 23C. All of the various locations of tether tensioning unit 500 relative to the spine segment and all of the various positions relative to the flexible tether 504 described above with lateral attachment are also possible with the posterior or posterior-lateral attachment location.

FIGS. 24A, B and C show one possible anchor screw 600 for fixing one end of a flexible tether (not shown) to the vertebral body (not shown). The anchor screw 600 is comprised at one end of a threaded body 602 for attachment to the vertebral body and at the other end a head 604 for securing the tether. The head 604 contains a set screw 610 and a clamping plate 608. The head 604 and clamping plate 608 define an opening 606 through which a flexible tether can be inserted. Once the tether has been positioned through the opening 606, the set screw 610 can be advanced against the clamping plate 608 until the clamping plate 608 compresses the tether against the base of the head 604 securing the tether and preventing any relative motion of the tether relative to the anchor screw 600. The head 604 can have an outer profile that is designed to be captured by a screw driving device for the purpose of advancing the anchor screw 600 into the vertebral body. Head 604, as shown in FIGS. 24A, B and C, has substantially square outer profile, but any type of profile that is commonly used for capture by a driving mechanism is possible, including but not limited to hexagonal, octagonal, and star-shaped.

FIGS. 25A-E show an alternative embodiment of an anchor screw 700 for fixing one end of a flexible tether, illustrated here as tether 720, to the vertebral body (not shown). The anchor screw 700 is comprised at one end of a threaded body 702 for attachment to the vertebral body and at the other end a head 704 for securing the tether. The head 704 contains a cam 706 and a cam pin 708. The head 704 and the cam 706 define an opening 710 through which a flexible tether can be inserted. As shown in FIG. 25E once the tether 720 is positioned through the opening 710, the cam 706 can rotate around the cam pin 708 to compress the tether 720 against the base 712 of the head 704 securing the tether 720 and preventing any relative motion of the tether 720 relative to the anchor screw 700. In general, tension applied to the tether in a direction away from the cam will cause the cam to further tighten on the tether, however, cam 706 may also include a biasing member (not shown) such as a torsional spring that biases the cam 706 against the base 712. The biased cam 706 will eliminate the opening 710 but would not be biased with a force sufficient to prevent the tether 720 from being advanced past the biased cam 706 in one direction. In this manner the anchor screw 700 will allow the tether 720 to be advance in one direction but will prevent the tether 720 from movement in the other.

FIG. 26 shows an embodiment of a bone anchor formed as a slip screw 800. The slip screw 800 is comprised of a threaded body 802 at one end and a head 804 at the other end. The head 804 has an opening 806 configured to allow through clearance of the tether (not shown). The slip screw 800 is used to guide the tether relative to the vertebral bodies between the two end attachment points of the tether.

FIG. 27 shows an alternative form of bone anchor as a slip staple 820. The slip staple 820 is comprised of one or more staple arms 822a-b at one end and a head 824 at the other end. The head 824 has an opening 826 configured to allow through clearance of the tether (not shown). The slip staple 820 is also used to guide the tether relative to the vertebral bodies between the two tether end attachment points. It is the surgeon's preference according to the patient's anatomic size and bone quality to use screws or staples for attachment of the spinal curvature modulation system to the patient's vertebral bodies. The staple attachment method can also be used to attach tether tensioning unit at one end of the tether and the anchor mechanism at the other. It is also the surgeon's preference to use slip screws 800 or slip staples 820 at the vertebral bodies located between the tether's two end attachment points, or to use anchor screws 700 at the vertebral bodies located between the tether's two end attachment points as well as at one anchor point. When slip screws 800 or slip staples 820 are used at the intermediate locations, the tension in the tether will be substantially constant between the two end attachment points. When anchor screws 700 are used at the intermediate attachment locations, the tension in the tether will vary between each of the separate anchor segments.

Figure 29A:
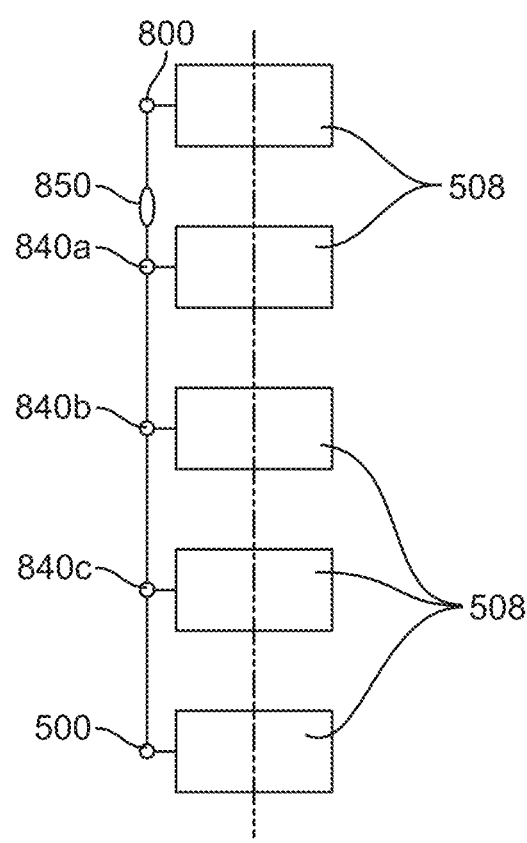
FIG. 29A is an illustration of a spine from a posterior view with an alternate embodiment of the spinal curvature modulation system attached laterally.
Figure 29B:
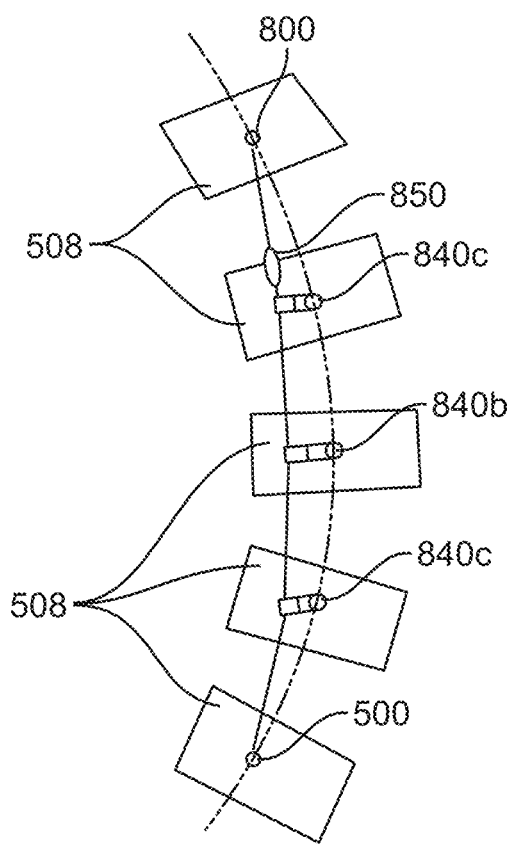
FIG. 29B is an illustration of a spine from a lateral view of the embodiment of the spinal curvature modulation system shown in FIG. 29A.

FIG. 28 shows an alternate embodiment of the slip screw 840. The slip screw 840 is comprised of a threaded body 842 at one end and a head 844 at the other end. The head 844 has an opening 846 configured to allow through clearance of the tether (not shown). The head 844 also has a slot 848 configured for positioning the opening 846 at varying distances relative to the threaded body 842. The varying distance of the opening 846 for guiding the tether can be beneficial for preserving spinal kyphosis as is illustrated in FIGS. 29A-B. The spinal curvature modulation system is designed to reduce the cobb angle of the spine as described herein.

In FIG. 29A the system is attached to vertebral bodies 508 with tether tensioning unit 500 attached at one end, the anchor screw 800 attached at the other end and slip screws 840a-c attached at intermediate levels. FIG. 29B shows the lateral view where the attachment points of the spinal curvature modulation system relative to the vertebral bodies 508 are shown to lie approximately on the midline (dashed line) of each vertebral body 508. The flexible tether 504 passes through the openings 846 of the slip screw 840, but the flexible tether 504 is not on the vertebral body 508 midline as the openings 846 are not lined up with the threaded bodies 842. This allows the flexible tether 504 to induce and/or preserve the kyphotic curvature of the spine in the sagittal plane which is a normal healthy curve while at the same time reducing the scoliotic curve in the coronal plane which is abnormal. The slip screws 840 located more in the middle of the spinal curvature modulation system can have openings 846 that are more offset from the midline than slip screws 840 located closer to the end attachment points. The openings 846 can be adjustably offset as illustrated in FIG. 28, or the openings 846 can be offset various non-adjustable fixed distances from the threaded body 842. The openings 846 can also be offset from one or more staple arms 822a-b rather than from a threaded body 842.

Also shown in FIGS. 29A and B is an optional tether stop 850. One or more tether stops 850 may be placed on the tether at selected locations to limit movement of one spine segment as relative to other segments across the treatment region. Tether stop 850 may be formed, for example, as a crimpable bead or ferrule and applied to the tether by the surgeon as needed at the time of installation of the tether and tensioning unit.

As previously described, the two end points, tether tensioning unit 500 and anchor device can be attached to the vertebral bodies by a threaded rod, a staple arm or any other common attachment mechanism including but not limited to bands, expandable rods, and the like. The connection between the anchor device and tether tensioning unit or the anchor device can be rigid as depicted in FIGS. 25-28 or the connections can allow some articulation or relative range of motion such as through a ball and socket type of connection.

Figure 30:
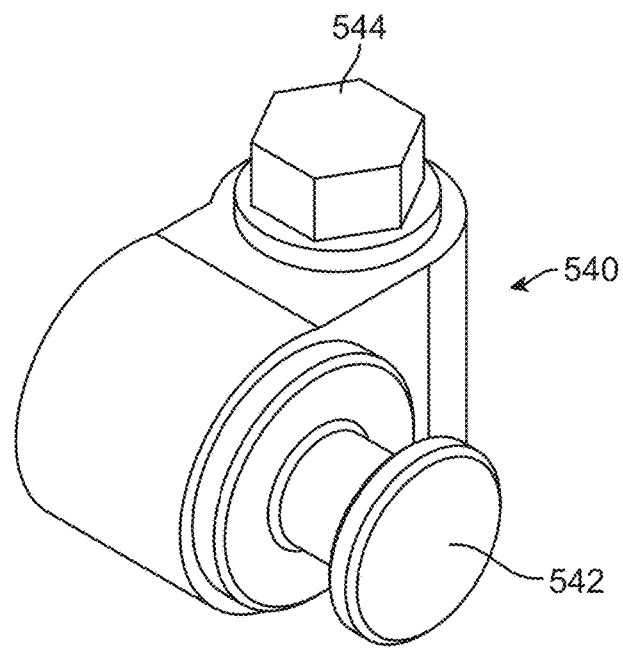
FIG. 30 is a perspective view of an alternate tension adjustment mechanism for the spinal curvature modulation system.

FIG. 30 shows another alternative tether tensioning unit 540, which is comprised of a tether interface spool 542 and a manual internal actuator 544. When the manual internal actuator 544 is rotated by an outside force (see, e.g., FIG. 11), it rotates the tether interface spool 542 through internal gears (e.g., FIGS. 4-11). The tool interface of manual internal actuator 544 is shown as an external hexagonal shape, but any commonly used driver shape can be used, including but not limited to an internal slot, a square shape or star shape, both of which could be either internal or external or the like.

Figures 31A, 31B:
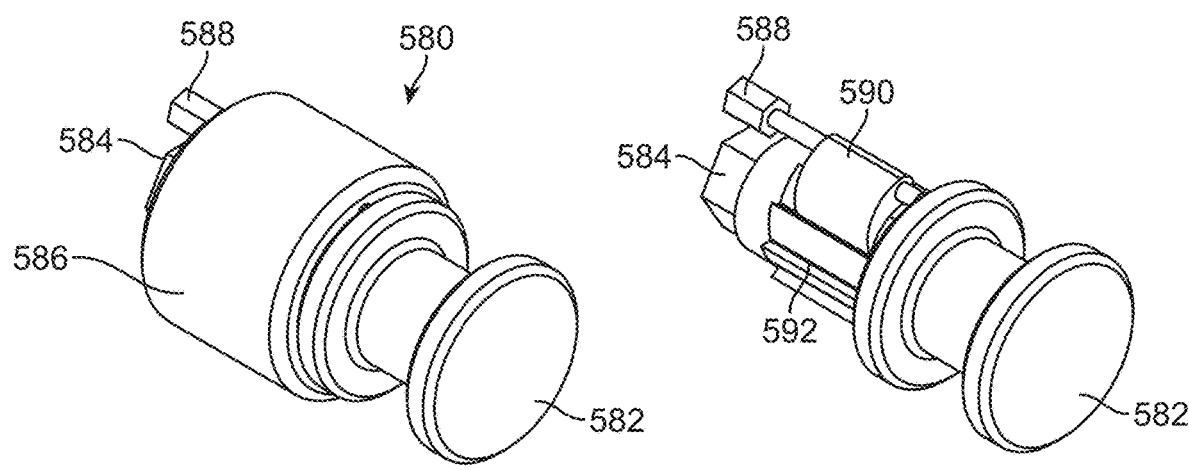
FIG. 31A is a perspective view of an alternate embodiment of a tension adjustment mechanism for the spinal curvature modulation system.
FIG. 31B is a perspective view of the tension adjustment mechanism of FIG. 31A with a housing removed.

FIGS. 31A-B show another embodiment of a tether tensioning unit 580 that is comprised of a manual internal actuator 584, a tether interface spool 582, a tension relief device 588, and a housing 586. When the manual internal actuator 584 is rotated by an outside force, it rotates the tether spool 582 either directly or through internal gears. In FIG. 31B the housing 586 has been removed to show an internal ratchet 592 and pawl 590 that allows the tether spool 582 to rotate in one forward direction to increase tension but prevents the tether spool 582 from rotating in the reverse direction to relieve tension. The tension relief device 588 can be actuated to raise the pawl 590 away from the ratchet 592 to allow the tether spool 582 to rotate in the reverse direction and release tension in the tether. This ratchet and tension release mechanism is not limited to the manually driven mechanism shown, but can also be included in the previously described magnet driven tension adjusting mechanisms. Likewise the actuation of the pawl 590 to allow reverse rotation of the tether spool 582 is not limited to manual actuation but also can be achieved through a second magnetic driven mechanism, or through an electrically driven mechanism such as but not limited to a solenoid.

The reduction of tether tension can be achieved by many other mechanisms in addition to this ratchet and pawl system. The tether tension can be reduced automatically when a sufficient tension is reached through a slip clutch type of mechanism. A slip clutch can be designed to release tether tension to prevent tension from becoming so great that it causes damage to spinal elements such as ligaments or intervertebral discs. Sensors as previously described can also be positioned at either end of the tether or anywhere along the length of the tether to measure the tether tension and prevent excessive tether tension by either sending a signal to automatically open a pawl and ratchet type tension release mechanism as previously described, or send a signal to an external control to inform the surgeon and/or the patient that excessive tension exists which should be reduced through the tension adjustment mechanism. The external controller can be paired wirelessly to other devices such as computers or smart phones so that a surgeon located remotely can be quickly notified. An internal sensor can be powered by an implanted battery or by power delivered through induction from an induction source located externally. The sensor can measure the tension in the tether directly, or it can measure the deflection the tether tension creates in the tether spool or anchor screw head or it could be located to measure the bending moment of the anchor screw's threaded body or staple arm. The sensor can also measure a different parameter not directly related to tether tension such as the number of rotations of the magnet. In one particular embodiment two Hall-effect sensors can be located in the external driver on either side of the driving magnet. These sensors can detect the rotation of the implant magnet by subtracting out the signal from the driving magnet. In this manner the external controller can collect data that the internal magnet is rotating as desired. The use of one or more Hall-effect sensors to measure the rotation of the implanted magnet can result in a noisy signal as the sensor's measurement of the more proximal control magnet will produce a much higher signal than the weaker signal from the distal implanted magnet. In addition to the use of two Hall-effect sensors to measure magnet rotation, the controller can also contain a current sensor to measure the amount of current that is being drawn by the motor rotating the control magnet. When the control magnet is initially rotated by the control motor but not magnetically coupled to the implanted magnet, a specific amount of current is drawn by the motor. When the control magnet couples with the implanted magnet, the load on the motor rotating the control magnet increases in order to rotate both the control magnet and the coupled magnet. The measurement of the current drawn by the control motor with a current sensor can be used to determine if the control magnet and the implanted magnet are coupled. On occasion there could be occurrences of magnet stalling due to an excessive load on the implanted magnet. Use of a current sensor will still show an increase in current drawn when the control magnet and implant magnet are coupled but stalled. The combination of a current sensor and one or more Hall-effect sensors can help to provide information of internal magnet rotation (and therefore tether tension adjustment) regardless of the different conditions such as magnet coupling or magnet stalling.

FIGS. 32A-B show a gear system 900 comprised of a globoid-shaped worm gear 902 and mating spur gear 904. The contour 906 of the worm gear 902 is higher on the ends and lower in the middle. This globoid shape allows a great force to be transferred from the worm gear to the spur gear for any given nominal diameter of worm and spur gears. The gear system 900 can be used in any of the previously described tension adjusting mechanisms to transfer the magnetic (or manual) driving force to the tether. This transfer of greater force is of particular importance in an implanted tension adjusting mechanism as it is important to keep the implant as small as possible while still delivering sufficient force to tension the tether to ensure proper adjustment of the curved spine.

Figure 33:
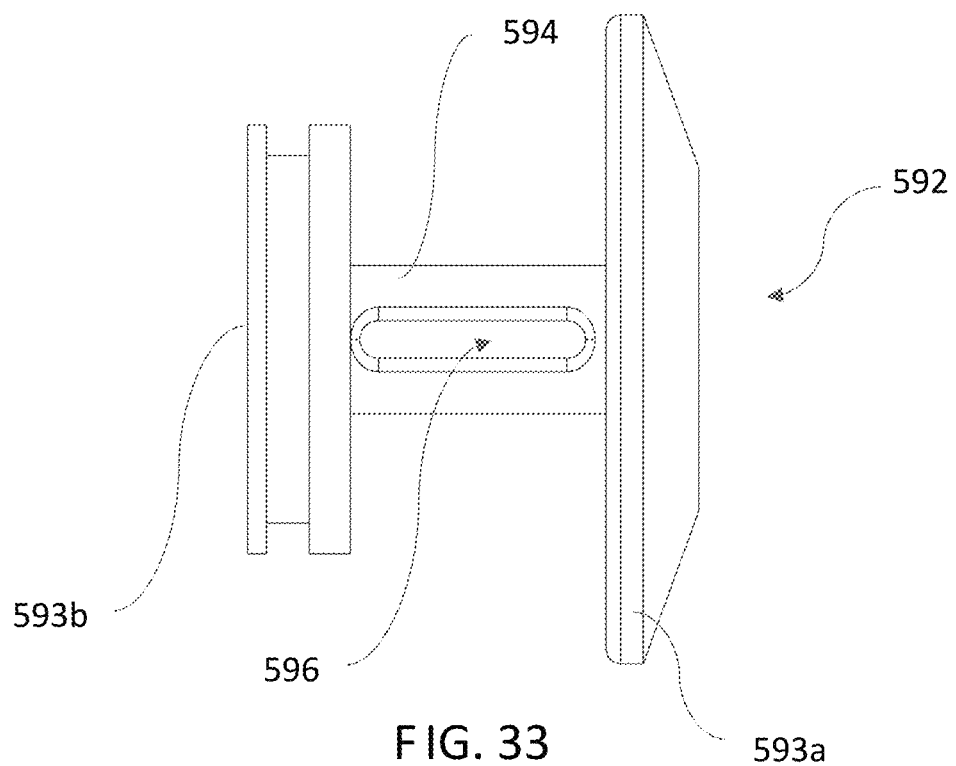
FIG. 33 is a perspective view of a further embodiment of the tether interface spool.

FIG. 33 shows a tether interface spool 592 for use with a tether tensioning unit such as the tether tensioning unit 500 shown in FIG. 17. Tether interface spool 592 comprises an alternative embodiment of tether interface 502, also shown in FIG. 17. The tether interface spool 592 is comprised of two spool end flanges 593a and 593b and a spool axel 594. The spool axel 594 contains an open slot 596. The open slot 596 is configured for a tether to pass through, such as the flexible tether 504 in FIG. 17. One end of the flexible tether 504 can pass through the open slot 596 in the tether interface spool 592 and that end can be fixed to the tether interface spool 592 with, for example, an adhesive. Alternately, the flexible tether 504 can be fixed to a stop or plug such as a rod or axel that is larger than the open slot 596. The flexible tether 504 can be crimped to the stop or plug. The flexible tether 504 can be attached to the stop or plug with adhesive. As the stop or plug is larger than the open slot 596 it prevents the flexible tether 504 attached to the stop or plug from passing through the open slot 596. The flexible tether 504 can also be wrapped around the stop or plug and attached to itself with adhesive or by sewing the flexible tether 504 to itself. The flexible tether 504 can also pass through the open slot 596 and wrap back over half of the spool axel 594. Both the portion of the flexible tether 504 entering the open slot 596 and the portion that is wrapped back over the spool axel 594 can be used as two tethers 142 such as those shown in FIG. 8. The two tethers 142 can be directed in opposite directions as shown in FIG. 8, or the two tethers 142 can be directed in the same direction to correct spinal deformities.

Figure 34:
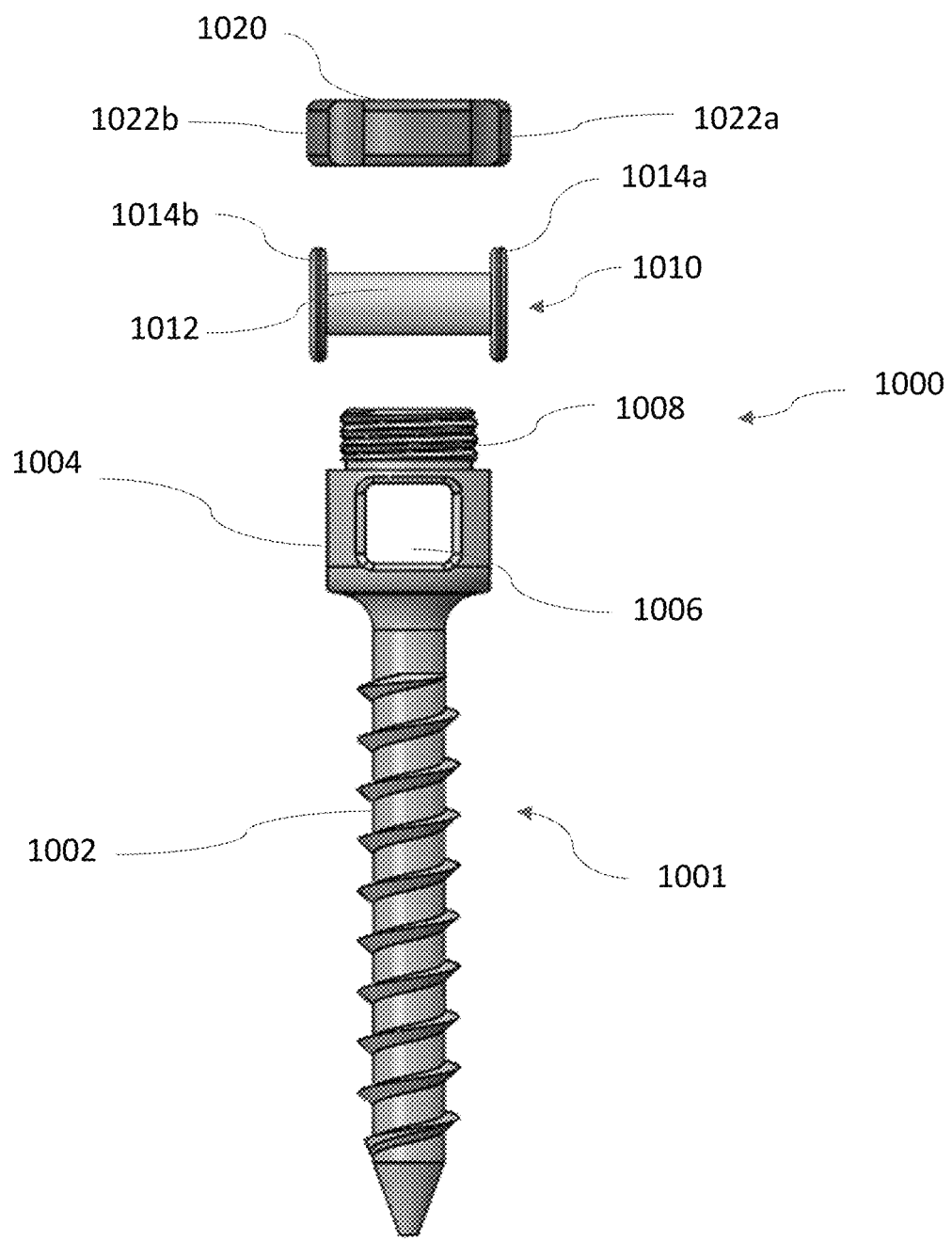
FIG. 34 is an exploded view of an alternative anchor screw for the spinal curvature modulation system.

FIG. 34 shows another possible anchor screw 1000 for fixing the tether at one end of the spinal curvature modulation system to a vertebral body. The anchor screw 1000 is comprised of a screw body 1001, a tether pin 1010, and a tether pin cap 1020. The anchor body 1001 is comprised at one end of a threaded body 1002 for attachment to the vertebral body and at the other end of a screw head 1004 for securing the tether. The screw head 1004 is comprised of an open window 1006 for passing the tether and a threaded top 1008 for engagement of the tether pin cap 1020. The tether pin 1010 is comprised of two pin flanges 1014a and 1014b and a pin axel 1012. The tether pin cap 1020 can include one or more indented grooves 1022a and 1022b that can be engaged with a tool for both holding the tether pin cap 1020 and for threading the tether pin cap 1020 onto the threaded top 1008 of the screw body 1001.

Figure 35A:
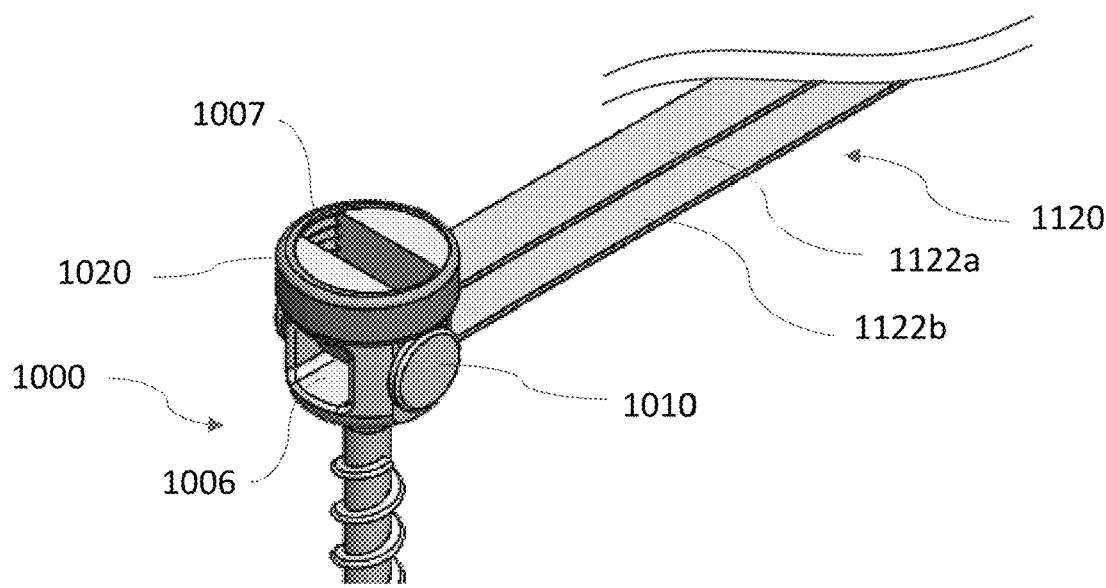
FIG. 35A is a perspective view of the anchor screw shown in FIG. 34.
Figure 35B:
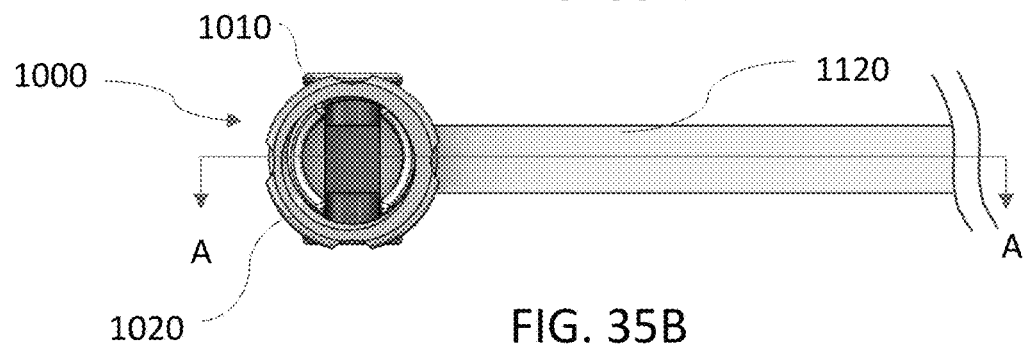
FIG. 35B is a top view of the anchor screw in FIG. 35A.
Figure 35C:
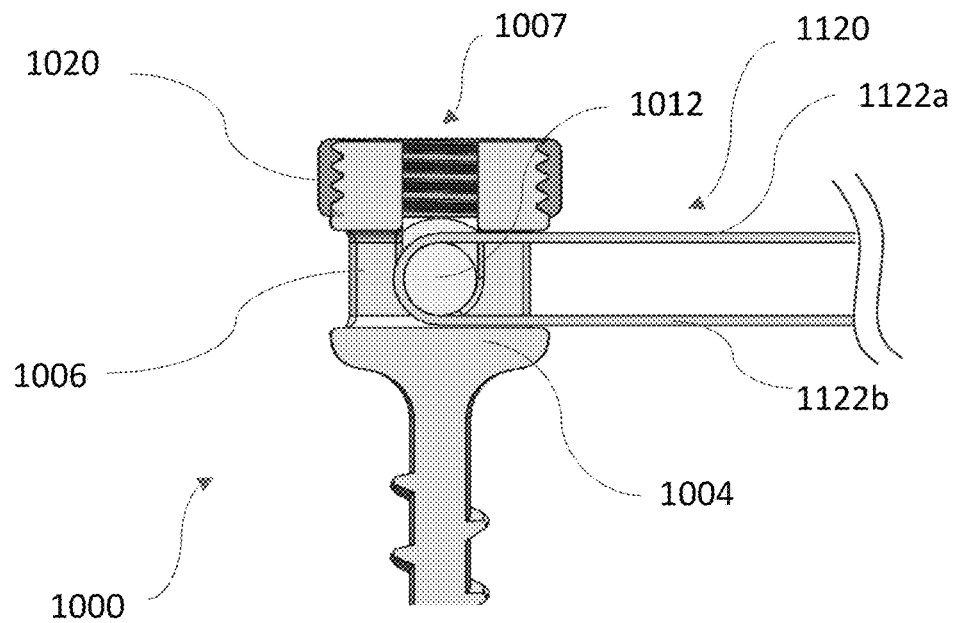
FIG. 35C is a cross-sectional view of the anchor screw in FIG. 35B through Line A-A.

FIGS. 35A, 35B, and 35C show the anchor screw 1000 engaging a flexible tether 1120. The flexible tether 1120 is comprised of two portions 1122a and 1122b. One portion 1122a passes through the open widow 1006 of the screw head 1004 and wraps around the pin axel 1012 of the tether pin 1010 and passes back through the open widow 1006 to form the second portion 1122b of the flexible tether 1120. The pin axel 1012 is seated in a top slot 1007 in the screw head 1004 with the pin flanges 1014a and 1014b on either side of the screw head 1004. The tether pin cap 1020 is threaded onto the threaded tip 1008 of the screw head 1004. This configuration of tether pin cap 1020, tether pin 1010 with pin flanges 1014a and 1014b, and top slot 1007 in the screw head 1004 constrain the tether pin 1010 to the anchor screw body 1001. The anchor screw 1000 provides a simple and quick method for securing a flexible tether 1120 comprised of two portions 1122a and 1122b to a vertebral body. The tether pin cap 1020 is shown as an open ring, but it can alternately have a top cover that has an engagement feature such as a slot for engaging a tool to rotate the tether pin cap 1020 onto the threaded top 1008 of the screw body 1001. The slot can be straight, hexagonal, star shaped, or any manner of configuration commonly used for engaging a rotating tool.

Figure 36:
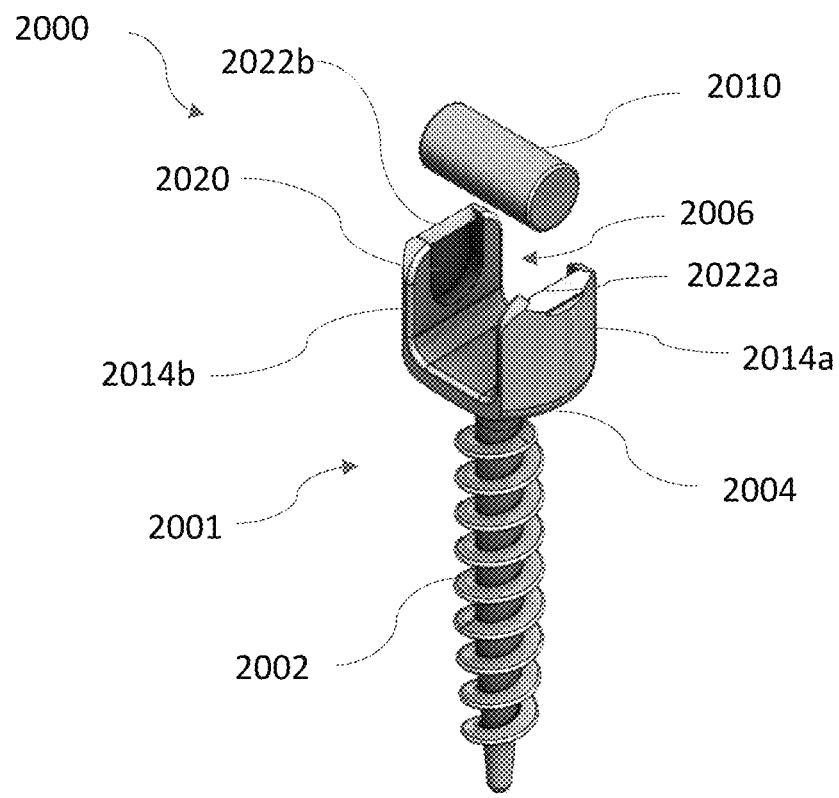
FIGS. 36, 37, 38, 39, and 40 are perspective views of alternative anchor screws for the spinal curvature modulation system.

FIGS. 36, 37, 38, 39, and 40 show alternative embodiments for anchor screws that provide a simple and quick method for securing a flexible tether 1120 comprised of two portions 1122a and 1122b to a vertebral body. FIG. 36 shows an alternate anchor screw 2000 comprised of a screw body 2001 and a tether pin 2010. The screw body 2001 is comprised at one end of a threaded body 2002 for attachment to the vertebral body and at the other end of a screw head 2004 for securing the tether. The screw head 2004 is comprised of an open slot 2006 and two side walls 2014a and 2014b on either side of the open slot 2006. Each of the side walls 2014a and 2014b have a retaining recess 2020, for example formed as a detent, on the inside to engage the ends of the tether pin 2010. The flexible tether 1120 wraps around the tether pin 2010, and then the tether pin 2010 is placed into the recesses 2020 between the two side walls 2014a and 2014b of the screw head 2004. The top of the two side walls 2014a and 2014b can have lead in chamfers 2022a and 2022b to help guide the tether pin 2010 into the detents 2020. Additionally, the tether pin 2010 can also have chamfers or radii at each end to help facilitate or guide the tether pin 2010 into the recesses 2020.

Figure 37:
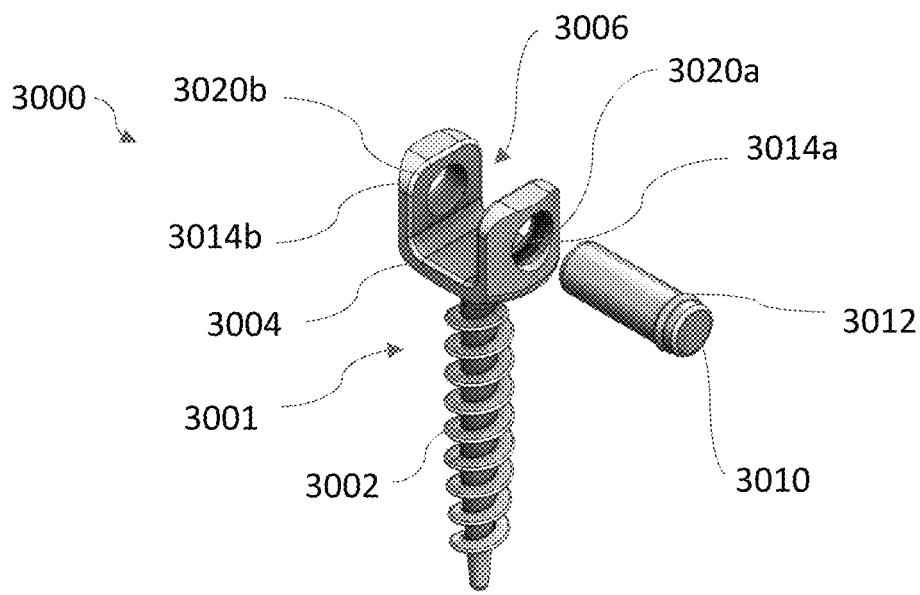

FIG. 37 shows an alternate anchor screw 3000 comprised of a screw body 3001 and a tether pin 3010. The screw body 3001 is comprised at one end of a threaded body 3002 for attachment to the vertebral body and at the other end of a screw head 3004 for securing the tether. The screw head 3004 is comprised of an open slot 3006 and two side walls 3014a and 3014b on either side of the open slot 3006. Each of the side walls 3014a and 3014b have a through hole 3020a and 3020b to engage the tether pin 3010. The first end of the tether pin 3010 is placed through the first through hole 3020a and into the open slot 3006. Then the flexible tether 1120 is guided into the open slot 3006 and wrapped around the tether pin 3010 and back out of the open slot 3006. The first end of tether pin 3010 is then placed into the second through hole 3020b. The tether pin 3010 can include one of more retaining gaskets 3012 that are configured to engage the inside of the through hole 3020a and/or 3020b to hold the tether pin 3010 in place relative to the screw body 3001. The retaining gasket 3012 does not have to hold the tether pin 3010 in place with a very large force because the tether pin 3010 will be firmly secured by the flexible tether 1120 once the flexible tether 540 is tensioned by the tether tensioning unit 500 (FIG. 17).

Figure 38:
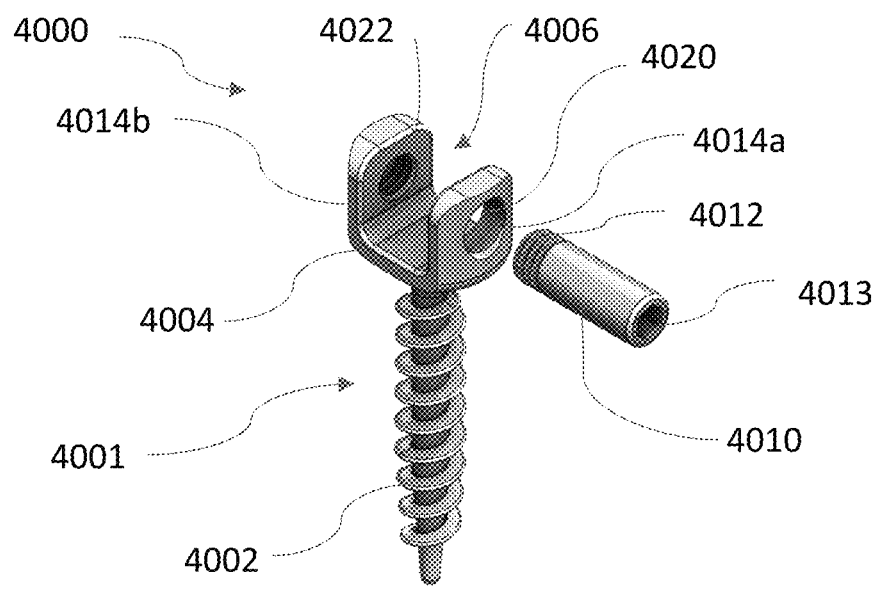

FIG. 38 shows an alternate anchor screw 4000 comprised of a screw body 4001 and a tether pin 4010. The screw body 4001 is comprised at one end of a threaded body 4002 for attachment to the vertebral body and at the other end of a screw head 4004 for securing the tether. The screw head 4004 is comprised of an open slot 4006 and two side walls 4014a and 4014b on either side of the open slot 4006. Side wall 4014a has a through hole 4020, and side wall 4014b has a threaded hole 4022. The first end of the tether pin 4010 has threads 4012 that are placed through the through hole 4020 and into the open slot 4006. Then the flexible tether 1120 is guided into the open slot 4006 and wrapped around the tether pin 4010 and back out of the open slot 4006. The first end of the tether pin 4010 is then screwed into the threaded hole 4022. The tether pin 4010 can include an engagement pocket 4013 at the second end face configured to engage a tool used to rotate the threaded pin 4010 into the threaded hole 4022. The threaded hole 4022 can be a blind threaded hole as shown in FIG. 38 or a through threaded hole.

Figure 39:
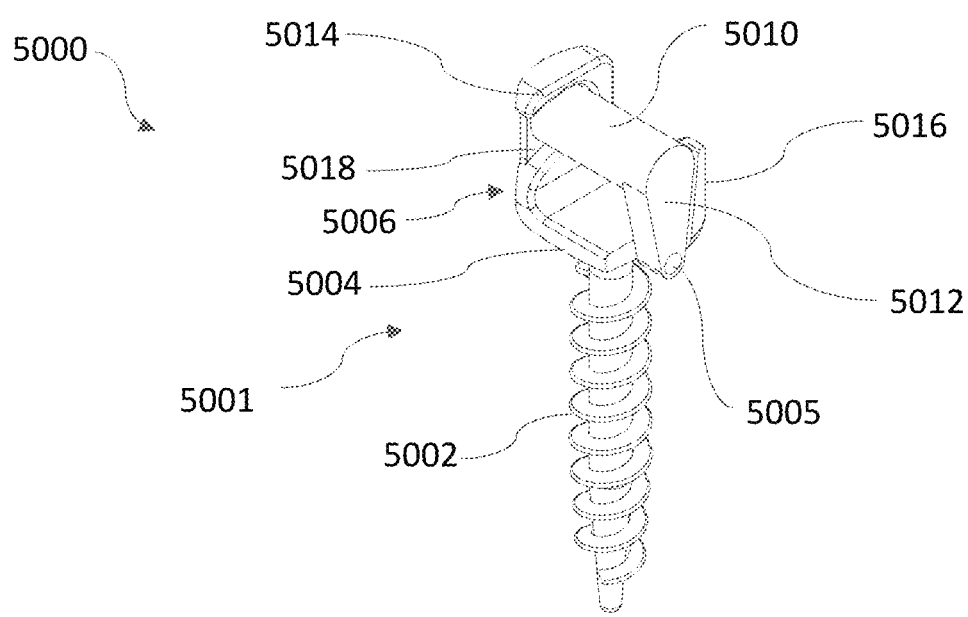

FIG. 39 shows an alternate anchor screw 5000 comprised of a screw body 5001 and a tether pin 5010. The screw body 5001 is comprised at one end of a threaded body 5002 for attachment to the vertebral body and at the other end of a screw head 5004 for securing the tether. The screw head 5004 is comprised of an open slot 5006 and two side walls 5014 and 5016 on either side of the open slot 5006. Side wall 5014 has a receptacle slot 5018 for receiving one end of the tether pin 5010. Side wall 5016 creates a stop that engages the extension wall 5012 at the other end of the tether pin 5010. The extension wall 5012 of the tether pin 5010 has a pivot pin 5005 at one end that is engaged in a pivot hole in the screw head 5004. The tether pin 5010 is pivoted away from the side wall 5016 such that the first end of the tether pin 5010 extends out of the receptacle slot 5018. The flexible tether 1120 is wrapped around the tether pin 5010 and then the tether pin 5010 is pivoted back such that the first end of the tether pin 5010 is captured in the receptacle slot 5018 and the extension wall 5012 of the tether pin 5010 is butted up against the side wall 5016 of the screw head 5004. The anchor screw 5000 is designed to anchor a flexible tether 1120 that extends away from the tether pin 5010 towards the extension wall 5016. Anchor screw 5000 would not anchor a flexible tether 1120 that extended in the other direction because a flexible tether 1120 extending away from the extension wall 5016 would pivot the tether pin 5010 away from the extension wall 5016 and open up the tether pin 5010 on the anchor screw 5000.

Figure 40:
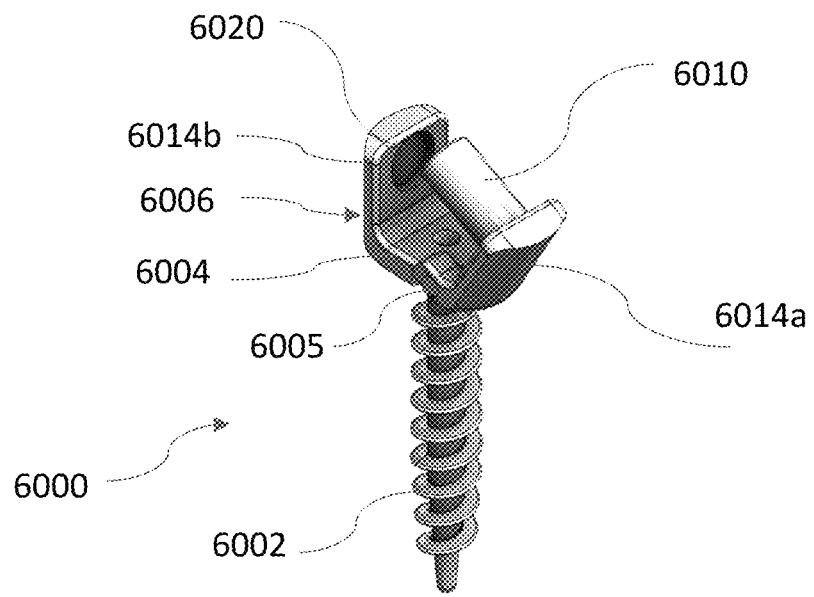

FIG. 40 shows an alternate anchor screw 6000 comprised at one end of a threaded body 6002 for attachment to the vertebral body and at the other end of a screw head 6004 for securing the tether 1120. The screw head 6004 is comprised of an open slot 6006 and two side walls 6014a and 6014b on either side of the open slot 6006. Side wall 6014b has a receptacle pocket 6020 for receiving one end of the tether pin 6010. Side wall 6014a has a pivot pin 6005 at one end that is engaged in a pivot hole in the screw head 6004. The tether pin 6010 is attached to side wall 6014a at the other end. The tether pin 6010 and the side wall 6014a pivot away from the side wall 6014*b* such that the first end of the tether pin 6010 extends out of the receptacle pocket 6020. The flexible tether 1120 is wrapped around the tether pin 6010 and then the tether pin 6010 and the side wall 6014*a* are pivoted back such that the first end of the tether pin 6010 is captured in the receptacle pocket 6020.

Figure 41:
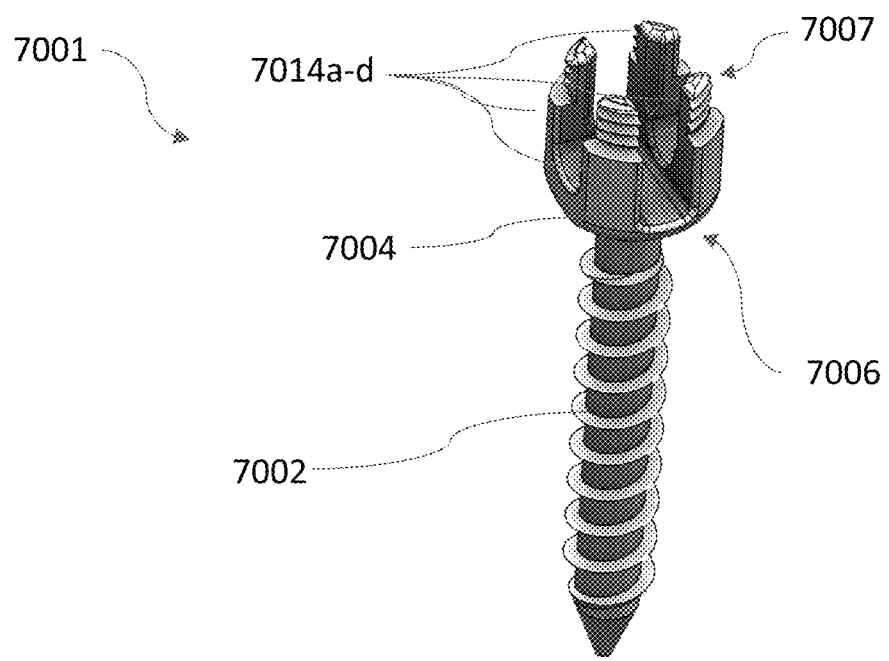
FIGS. 41, 42, and 43 are perspective views of alternative slip screws.

FIG. 41 shows another possible screw body 7001 comprised at one end of a threaded body 7002 for attachment to the vertebral body and at the other end of a screw head 7004 for securing the tether 1120. The screw body 7001 of FIG. 41 is similar to the screw body 1001 of FIG. 34 in that the screw body 7001 of FIG. 41 is configured to work with tether pin 1010, and a tether pin cap 1020, such as shown in FIG. 34. The screw head 7004 is comprised of an open slot 7006 for receiving the tether and an orthogonal slot 7007 for receiving the tether pin 1010. The open slot 7006 and orthogonal slot 7007 are bordered by 4 threaded pillars 7014*a-d* which are configured to engagement of the tether pin cap 1020. The open slot 7006 receives the flexible tether 1120 and tether pin 1010 as a combined unit from above without having to pass the flexible tether 1120 through the open window 1006 and then around the tether pin 1010 as is required for the screw body in FIG. 34. Having an open slot 7006 allows the surgeon to easily attach the tether to the screw body 7001.

Figure 42:
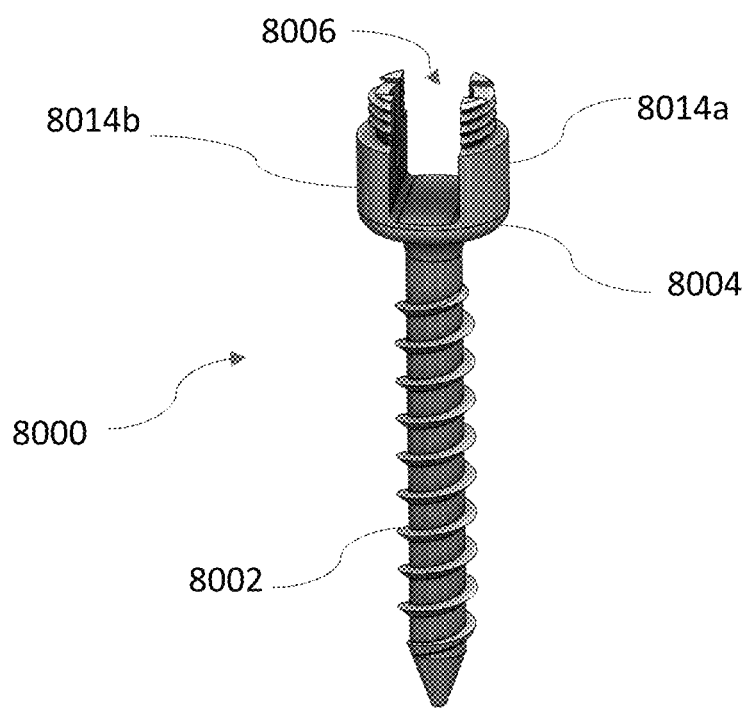

It is also desirable for the surgeon to attach the tether to a slip screw from an open top configuration. FIG. 42 shows a slip screw body 8000 comprised at one end of a threaded body 8002 for attachment to the vertebral body and at the other end of a screw head 8004 for guiding the tether. The screw head 8004 is comprised of an open slot 8006 and two side walls 8014*a* and 8014*b* on either side of the open slot 8006. The top ends of side walls 8014*a* and 8014*b* are threaded to engage a top cap such as the tether pin cap 1020 shown in FIG. 34. The slip screw body 8000 is attached to a vertebral body and then the flexible tether 1120 is placed into the open slot 8006. The flexible tether 1120 is captured in the open slot 8006 by threading the tether pin cap 1020 onto the threaded top ends of the side walls 8014*a* and 8014*b*. The open slot 8006 and the tether pin cap 1020 combine to create an opening that constrains but also provides clearance for the flexible tether 1120. This allows the slip screw to guide the flexible tether 1120 relative to the vertebral bodies between the two end attachment points of the flexible tether 1120.

Figure 43:
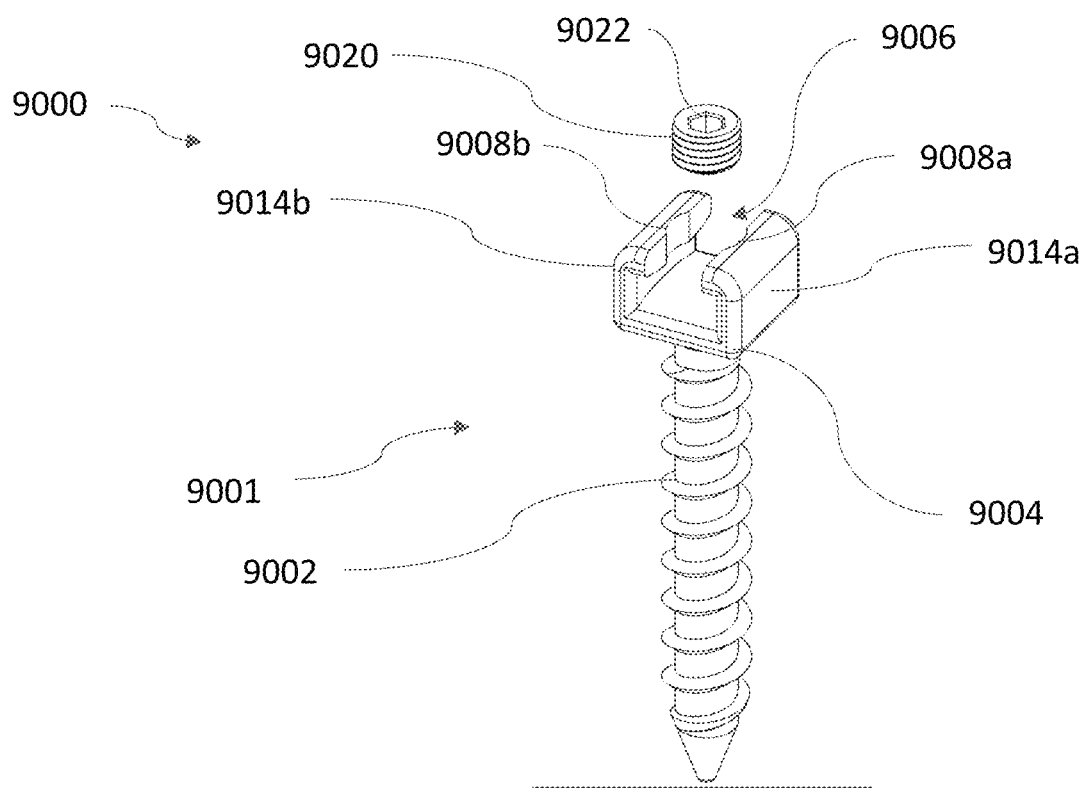

FIG. 43 shows an alternate slip screw 9000 comprised of a screw body 9001 and a screw cap 9020. The screw body 9001 is comprised at one end of a threaded body 9002 for attachment to the vertebral body and at the other end of a screw head 9004 for guiding the tether. The screw head 9004 is comprised of an open slot 9006 and two side walls 9014*a* and 9014*b* on either side of the open slot 9006. The top ends of side walls 9014*a* and 9014*b* are comprised of female threads to engage the male threads of the screw cap 9020. The slip screw body 9000 is attached to a vertebral body and then the flexible tether 1120 is placed into the open slot 9006. The flexible tether 1120 is captured in the open slot 9006 by threading the screw cap 9020 into the female threaded top ends of the side walls 9014*a* and 9014*b*. The thread tool receptacle 9022 in one end of the screw cap 9020 is configured to receive a threading tool for threading the screw cap 9020 into the screw head 9004.

In a further alternative embodiment, an anchor screw may be configured substantially as shown in FIG. 36, 37 or 38, except that the tether pin is integrally formed with the head portion sidewalls such that in this alternative embodiment the anchor screw is a unitary construction. Such an embodiment may be employed as an end anchor for the flexible tether by passing one end under the pivot pin and wrapping the flexible tether around the pivot pin, substantially as shown in FIG. 35C for example. Also, the same embodiment may be used as a slip/guide anchor by passing both ends of the flexible tether underneath the tether pin.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A spinal curve modulation system for treating spinal curvature along
   a treatment region of the spine, comprising:
   a flexible tether of sufficient length to extend across the treatment region of the spine including across at least three adjacent vertebral bodies in a cranial-caudal direction;
   plural first bones anchors configured to be fixed to one or more first vertebra and to the flexible tether and further configured for fixed attachment to the flexible tether at plural locations along the flexible tether;
   a tether tensioning unit comprising a tether interface member rotatable around a rotation axis and a remotely operable rotary drive operatively linked to the tether interface member to adjust tension in the flexible tether, said tension applied to the flexible tether in a direction perpendicular to the rotation axis; and
   at least one second bone anchor having a longitudinal axis perpendicular to the rotation axis and configured to fix the tether tensioning unit to a vertebra across the treatment region from at least one first bone anchor;

wherein said tether tensioning unit is actuatable to adjust tension in the flexible tether without surgically exposing the flexible tether, said first bone anchors or said at least one second bone anchor.

2. The spinal curve modulation system of claim 1, wherein said first bone anchors comprise:
a threaded body portion with a tip configured to penetrate bone;
a head portion disposed on the threaded body portion opposite the tip, wherein said head portion has a threaded top, and defines an open window for passing the flexible tether therethrough and an upwardly open slot extending across the head portion transverse to the open window;
a tether pin configured to be received in said upwardly open slot extending across the open window; and
a tether pin cap with an internal thread configured to engage said threaded top and retain the tether pin in said upwardly open slot.

3. The spinal curve modulation system of claim 2, wherein said open window is formed as a second upwardly open slot such that the head portion comprises four threaded pillars, whereby the tether pin with the flexible tether wrapped therearound may be placed in the second upwardly open slot to secure the flexible tether thereto without having to pass an end of the flexible tether through the open window.

4. The spinal curve modulation system of claim 1, wherein said first bone anchors comprise:
a threaded body portion with a tip configured to penetrate bone;
a head portion disposed on the threaded body portion opposite the tip, wherein said head portion comprises two opposed side walls defining an open slot therebetween; and
a tether pin extending across the open slot between the opposed side wall.

5. The spinal curve modulation system of claim 4, wherein:
said side walls each have an inwardly facing recess; and
the tether pin is removable and configured to be received in and retained by said inwardly facing recesses.

6. The spinal curve modulation system of claim 4, wherein:
said side walls define transverse openings; and
the tether pin is removable and configured to be received in and retained by said transverse openings.

7. The spinal curve modulation system of claim 6, wherein the tether pin includes at least one retaining gasket on at least one end, said retaining gasket configured to engage an inner circumference of at least one said transvers openings to retain the tether pin therein.

8. The spinal curve modulation system of claim 6, wherein the tether pin includes an external thread on at least one end and at least one said transverse opening is formed with an internal thread configured to mate with the tether pin external thread.

9. The spinal curve modulation system of claim 1, wherein said first bone anchors comprise:
a threaded body portion with a tip configured to penetrate bone;
a tether pin with a first end, a central portion configured to permit the flexible tether to be wrapped therearound, and a second end with a radially directed side wall; and
a head portion disposed on the threaded body portion opposite the tip configured to receive and support the tether pin, wherein-said head portion comprises first and second side walls forming an open slot therebetween with a receptacle slot formed in the first side wall opening towards a side of the head portion and an upwardly extending stop formed by the second wall,
the tether pin first end is configured to be received in said receptacle slot,
a pivot pin is disposed on the tether pin radially directed side wall spaced from the central portion of the tether pin, and
a pivot hole configured to receive the pivot pin is formed in the second side wall adjacent a lower end of the upwardly extending stop;
whereby the flexible tether is secured by wrapping around the tether pin central portion and the tether pin pivoted such that the first end of the tether pin is captured in the receptacle slot and the extension wall of the tether pin is butted up against the side wall of the head portion.

10. The spinal curve modulation system of claim 1, wherein said first bone anchors comprise:
a threaded body portion with a tip configured to penetrate bone;
a head portion disposed on the threaded body portion opposite the tip, wherein said head portion comprises first and second side walls forming an open slot therebetween with the first side wall defining a receptacle pocket and the second side wall is pivotable outward with respect to the open slot; and
a tether pin disposed on the second side wall extending towards the first side wall and configured to be received in the receptacle pocket of the first side wall.

11. The spinal curve modulation system of claim 1, wherein said tether interface comprises a tether interface spool engageable with the rotary drive, the tether interface spool having two spool end flanges with a spool axel disposed therebetween, the spool axel defining an open slot configured for the flexible tether to pass through.

12. The spinal curve modulation system of claim 11, wherein the flexible tether has sufficient length to pass through said slot and wrap around at least a portion of the spool axel with both tether ends secured at a common bone anchor.

13. The spinal curve modulation system of claim 1, further comprising at least one tether guide having a bone anchor and a guide portion configured to slidably receive the flexible tether, wherein the guide portion comprises a head defining an opening through which the flexible tether may slide along a longitudinal direction.

14. The spinal curve modulation system of claim 13, wherein the guide portion of the tether guide comprises the head formed with opposed side walls defining an open slot therebetween, the head having screw external threads at an upper end configured to receive a threaded cap thereon.

15. The spinal curve modulation system of claim 13, wherein the guide portion of the tether guide comprises the head formed with opposed side walls defining an open slot therebetween, each said side wall including a portion of a female threaded hole such that a threaded plug can be screwed in between the opposed side walls.

16. A bone anchor for securing a flexible tether to exert force on a bone, comprising:
a threaded body portion with a tip configured to be screwed into bone; and
a head portion disposed on the threaded body portion opposite the tip;

wherein the head portion comprises means for securing the flexible tether, and said means for securing the tether comprises:
a threaded top formed on the head portion;
an open window defined in the head portion under the threaded top for passing the tether therethrough;
an upwardly open slot extending across the head portion transverse to the open window;
a tether pin configured to be received in said upwardly open slot extending across the open window; and
a tether pin cap with an internal thread configured to engage said threaded top and retain the tether pin in said upwardly open slot.

17. The bone anchor of claim 16, wherein said open window is formed as a second upwardly open slot such that the head portion comprises four threaded pillars, whereby the tether pin with the flexible tether wrapped therearound may be placed in the second upwardly open slot to secure the flexible tether thereto without having to pass the flexible tether through the open window.

18. A bone anchor for securing a flexible tether to exert force on a bone, comprising:
a threaded body portion with a tip configured to be screwed into bone; and
a head portion disposed on the threaded body portion opposite the tip;
wherein the head portion comprises means for securing the flexible tether;
wherein said means for securing the tether comprises:
first and second side walls formed in the head portion defining an open slot therebetween with a receptacle slot formed in the first side wall opening towards a side of the head portion and an upwardly extending stop formed by the second wall;
a tether pin with a first end, a central portion configured to permit the flexible tether to be wrapped therearound, and a second end with a radially directed side wall, wherein the tether pin first end is configured to be received in said receptacle slot;
a pivot pin disposed on said radially directed side wall spaced from the central portion of the pivot pin; and
a pivot hole configured to receive the pivot pin formed in the second side wall adjacent a lower end of the upwardly extending stop;
whereby the flexible tether is secured by wrapping around the tether pin central portion and the tether pin pivoted such that the first end of the tether pin is captured in the receptacle slot and the extension wall of the tether pin is butted up against the side wall of the head portion.

19. A bone anchor for securing a flexible tether to exert force on a bone, comprising:
a threaded body portion with a tip configured to be screwed into bone; and
a head portion disposed on the threaded body portion opposite the tip;
wherein the head portion comprises means for securing the flexible tether;
wherein said means for securing the tether comprises:
first and second side walls formed in the head portion defining an open slot therebetween with the first side wall defining a receptacle pocket and the second side wall pivotable outward with respect to the open slot; and
a tether pin disposed on the second side wall extending towards the first side wall and configured to be received in the receptacle pocket of the first side wall.

20. A method of treating an abnormal spinal curvature along a treatment region of the spine, comprising:
providing surgical access to the treatment region of the spine, the treatment region extending along the spine in a generally cranial-caudal direction and spanning at least three adjacent vertebrae;
fixing a first bone anchor on a selected vertebra at a first end of the treatment region;
fixing a second bone anchor having a longitudinal axis on a selected second vertebra spaced across the treatment region from the first bone anchor;
fixing at least one third bone anchor on a selected vertebra between the first and second bone anchors;
attaching a tether tension adjustment mechanism to the second bone anchor after fixing the second bone anchor to the selected second vertebra;
extending a flexible tether between said tension adjustment mechanism and the first bone anchor;
fixing the flexible tether to the at least one third bone anchor;
manipulating said tension adjustment mechanism to initially tension the flexible tether so as to reposition vertebrae across the treatment region;
closing the surgical access to the treatment region of the spine; and
post-operatively, subsequent to closing the surgical access and without reopening or creating new surgical access to the flexible tether or bone anchors, manipulating said tension adjustment mechanism in vivo to periodically adjust tension in the flexible tether, and
wherein the tether tension adjustment mechanism comprises a rotatable tether interface spool with a spool axel defining a slot, and said step of extending the flexible tether between said tension adjustment mechanism and the first bone anchor comprises passing an end of the flexible tether through said spool axel slot and wrapping the flexible tether around at least a portion of the spool axel.

21. The method of claim 20, wherein:
said post-operatively manipulating said rotary member comprises driving the rotary member with a wirelessly controllable motor under control of a remote, wireless controller external to the body; and
said wirelessly controllable motor comprises a magnetic motor and said manipulating the wirelessly controllable motor comprises rotating at least one magnet in said remote, wireless controller.

* * * * *